United States Patent
Amanai et al.

(10) Patent No.: US 11,067,788 B2
(45) Date of Patent: Jul. 20, 2021

(54) BRIGHT RELAY OPTICAL SYSTEM, AND OPTICAL SYSTEM FOR RIGID ENDOSCOPE AND RIGID ENDOSCOPE USING THE SAME

(71) Applicant: OLYMPUS CORPORATION, Hachioji (JP)

(72) Inventors: Takahiro Amanai, Hachioji (JP); Tsutomu Uzawa, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 210 days.

(21) Appl. No.: 16/221,569

(22) Filed: Dec. 16, 2018

(65) Prior Publication Data
US 2019/0121117 A1  Apr. 25, 2019

Related U.S. Application Data

(63) Continuation of application No. PCT/JP2016/068167, filed on Jun. 17, 2016.

(51) Int. Cl.
*G02B 23/24* (2006.01)
*G02B 23/26* (2006.01)
(Continued)

(52) U.S. Cl.
CPC ............ *G02B 23/243* (2013.01); *A61B 1/055* (2013.01); *A61B 1/0661* (2013.01); *A61B 1/07* (2013.01);
(Continued)

(58) Field of Classification Search
CPC .. G02B 23/243; G02B 13/00; G02B 13/0095; G02B 23/26; G02B 27/0056;
(Continued)

(56) References Cited

U.S. PATENT DOCUMENTS 4,693,568 A * 9/1987 Takahashi .......... A61B 1/00096
359/772
5,093,719 A * 3/1992 Prescott ............... G02B 3/0087
348/65
(Continued)

FOREIGN PATENT DOCUMENTS

JP   S61077819 A   4/1986
JP   H07005377 A   1/1995
(Continued)

OTHER PUBLICATIONS

International Preliminary Report on Patentability (IPRP) (and English language translation thereof) and Written Opinion dated Dec. 27, 2018 issued in counterpart International Application No. PCT/JP2016/068167.
(Continued)

*Primary Examiner* — Arnel C Lavarias
(74) *Attorney, Agent, or Firm* — Holtz, Holtz & Volek PC

(57) ABSTRACT

A relay optical system includes an object-side lens which is disposed nearest to an object, an image-side lens which is disposed nearest to an image, and a cemented lens having a positive refractive power. The object-side lens has a positive refractive power and is disposed such that a convex surface is directed toward an object side. The image-side lens has a positive refractive power and is disposed such that a convex surface is directed toward an image side. A plurality of the cemented lenses is disposed between the object-side lens and the image side lens and the following conditional expression (1) is satisfied:

$$0.04 < Gce/Drel < 0.4 \qquad (1)$$

where,
Gce denotes the smallest of intervals of adjacent cemented lenses, and
(Continued)

Drel denotes a distance from an object plane up to an image plane of the relay optical system.

16 Claims, 24 Drawing Sheets

(51) Int. Cl.
*G02B 13/00* (2006.01)
*A61B 1/07* (2006.01)
*A61B 1/055* (2006.01)
*A61B 1/06* (2006.01)
*G02B 27/00* (2006.01)

(52) U.S. Cl.
CPC ......... *G02B 13/00* (2013.01); *G02B 13/0095* (2013.01); *G02B 23/26* (2013.01); *G02B 27/0056* (2013.01)

(58) Field of Classification Search
CPC ................ G02B 23/2446; G02B 23/24; G02B 23/2407; A61B 1/055; A61B 1/0661; A61B 1/07; A61B 1/00163; A61B 1/00195; A61B 1/002; A61B 1/04
USPC ....... 359/434, 362, 363, 368, 435, 558, 566, 359/569, 576; 600/101, 109, 160, 162, 600/181
See application file for complete search history.

(56) References Cited

U.S. PATENT DOCUMENTS

| | | | | |
|---|---|---|---|---|
| 5,142,410 A * | 8/1992 | Ono | ................... | G02B 23/2446 359/434 |
| 5,651,759 A * | 7/1997 | Leiner | ................ | A61B 1/00179 600/128 |
| 5,684,629 A * | 11/1997 | Leiner | .................... | A61B 1/002 359/362 |
| 5,861,987 A | 1/1999 | Nakamura et al. | | |
| 6,490,085 B1 * | 12/2002 | Zobel | ................ | G02B 23/2446 359/435 |
| 7,002,741 B2 * | 2/2006 | Lei | .................... | G02B 13/0095 359/362 |
| 7,515,335 B2 * | 4/2009 | Tomioka | ............ | G02B 23/2446 359/434 |
| 2013/0194667 A1 | 8/2013 | Inoue | | |

FOREIGN PATENT DOCUMENTS

| | | |
|---|---|---|
| JP | H08122666 A | 5/1996 |
| JP | 4470142 B2 | 6/2010 |
| JP | 5307952 B2 | 10/2013 |

OTHER PUBLICATIONS

International Search Report (ISR) dated Aug. 30, 2016 issued in International Application No. PCT/JP2016/068167.
Written Opinion dated Aug. 30, 2016 issued in International Application No. PCT/JP2016/068167.

* cited by examiner

BRIGHT RELAY OPTICAL SYSTEM, AND OPTICAL SYSTEM FOR RIGID ENDOSCOPE AND RIGID ENDOSCOPE USING THE SAME

CROSS-REFERENCE TO RELATED APPLICATION

The present application is a continuation application of International Application No. PCT/JP2016/068167 filed on Jun. 17, 2016, the entire contents of which are incorporated herein by reference.

BACKGROUND OF THE INVENTION

Field of the Invention

The present invention relates to a bright relay optical system, and an optical system for rigid endoscope and a rigid endoscope using the same.

Description of the Related Art

In recent years, in a diagnosis using a rigid endoscope, an improvement in a diagnostic accuracy is sought. In order to fulfil this requirement, in the rigid endoscope, an ability to observe an object with a high resolution and an ability to acquire an image of the object with a high image quality have been sought.

An observation and an acquisition of the image of the object are carried out via an optical system for rigid endoscope disposed in the rigid endoscope. In the acquisition of the image of the object, a camera head for instance is connected to the optical system for rigid endoscope. In the camera head, a CCD (Charge Coupled Device) or a CMOS (Complementary Metal Oxide Semiconductor) is used as an image pickup element.

The optical system for rigid endoscope includes an objective lens, an eyepiece, and a plurality of relay optical systems. The plurality of relay optical systems is disposed between the objective lens and the eyepiece.

An image of the object (hereinafter, referred to as 'primary image') is formed by the objective lens. The primary image becomes an inverted image, or in other words, becomes an image in which the object is inverted in a vertical direction. In a relay optical system, the primary image is relayed. An image formed by a relay optical system is also an inverted mage. The primary image is an inverted image and an image relayed is also an inverted image. Therefore, an image, after being relayed once, becomes an erected image. In the rigid endoscope, usually, an erected image is to be observed or captured. The primary image being an inverted image, the number of relay optical system becomes odd.

In Japanese Patent No. 5307952 Publication, a relay optical image which includes a front unit, an intermediate unit, and a rear unit has been disclosed. In this relay optical system, a diffractive optical element is disposed in the intermediate unit.

In Japanese Patent No. 4470142 Publication, a relay optical system which includes a first lens unit and a second lens unit has been disclosed. In this relay optical system, a diffractive optical element is disposed in both the first lens unit and the second lens unit.

SUMMARY OF THE INVENTION

A relay optical system according to at least some embodiments of the present invention comprises:

an object-side lens which is disposed nearest to an object,
an image-side lens which is disposed nearest to an image, and
a cemented lens having a positive refractive power, wherein
the object-side lens has a positive refractive power and is disposed such that a convex surface is directed toward an object side, and
the image-side lens has a positive refractive power, and is disposed such that a convex surface is directed toward an image side, and
a plurality of the cemented lenses is disposed between the object-side lens and the image-side lens, and
the following conditional expression (1) is satisfied:

$$0.04 < Gce/Drel < 0.4 \quad (1)$$

where,
Gce denotes the smallest interval of intervals of adjacent cemented lenses, and
Drel denotes a distance from an object plane up to an image plane of the relay optical system.

An image relay unit according to at least some embodiments of the present invention comprises:
a plurality of relay optical systems, wherein
at least one relay optical system of the plurality of relay optical systems is the abovementioned relay optical system.

An image relay unit according to at least some embodiments of the present invention comprises:
a predetermined relay optical system, and
a relay optical system consisting of lenses, wherein
the number of the relay optical systems consisting of lenses is larger than the number of the predetermined relay optical systems, and
the predetermined relay optical system is the abovementioned relay optical system, and
the following conditional expression (10) is satisfied:

$$0.05 < NAI \times FLdoe/Dreall < 1.5 \quad (10)$$

where,
NAI denotes an image-side numerical aperture of the relay optical system,
FLdoe denotes a focal length of the diffractive optical element, and
Dreall denotes a distance from an object plane up to an image plane of the image relay unit.

An optical system for rigid endoscope according to at least some embodiments of the present invention comprises:
an objective optical system, and
an image relay unit which is disposed on an image side of the objective optical system, wherein
the image relay unit is the abovementioned image relay unit.

A rigid endoscope according to at least some embodiments of the present invention comprises:
the abovementioned optical system for rigid endoscope, and
an image pickup element which captures an image formed by the image relay unit.

A rigid endoscope according to at least some embodiments of the present invention comprises:
the abovementioned optical system for rigid endoscope, and
an illuminating unit for illuminating an object to be observed.

DETAILED DESCRIPTION OF THE INVENTION

Figure 1:
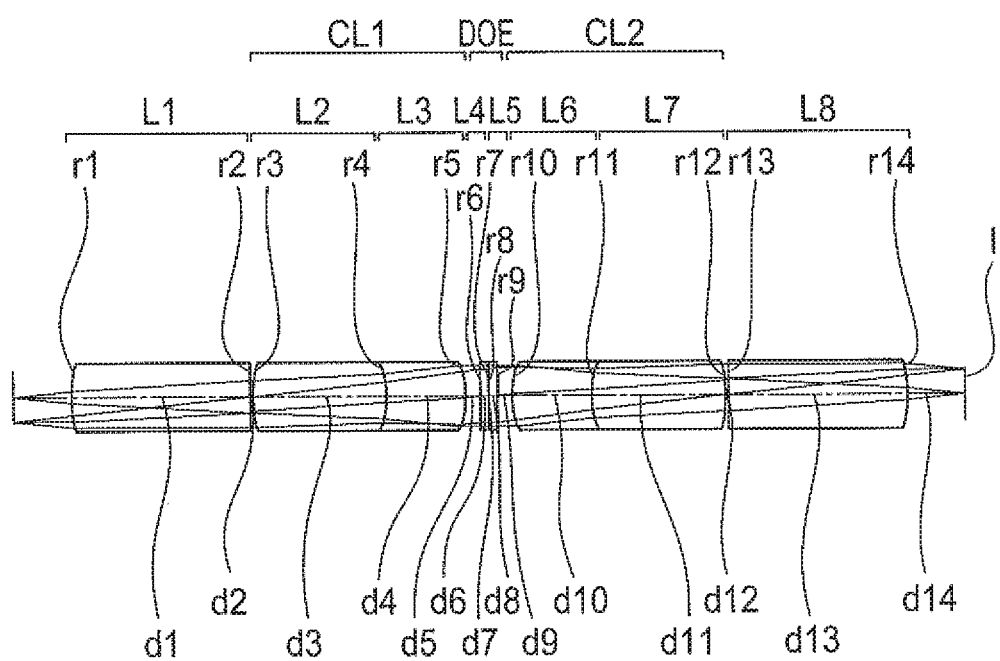
FIG. 1 is a lens cross-sectional view of a relay optical system of an example 1.
Figure 2:
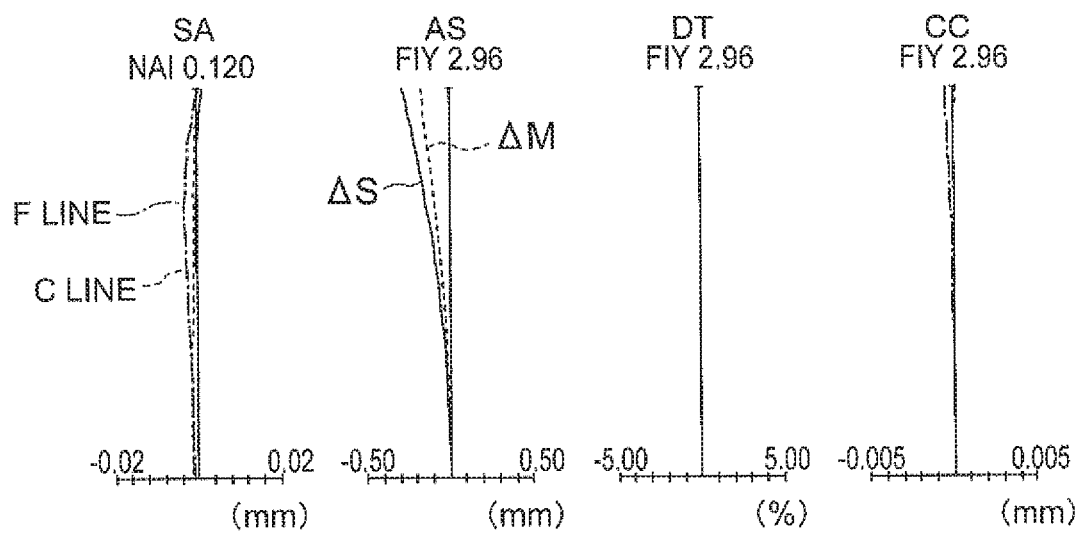
FIG. 2A, FIG. 2B, FIG. 2C, and FIG. 2D are aberrations diagrams of the relay optical system of the example 1.
Figure 3:
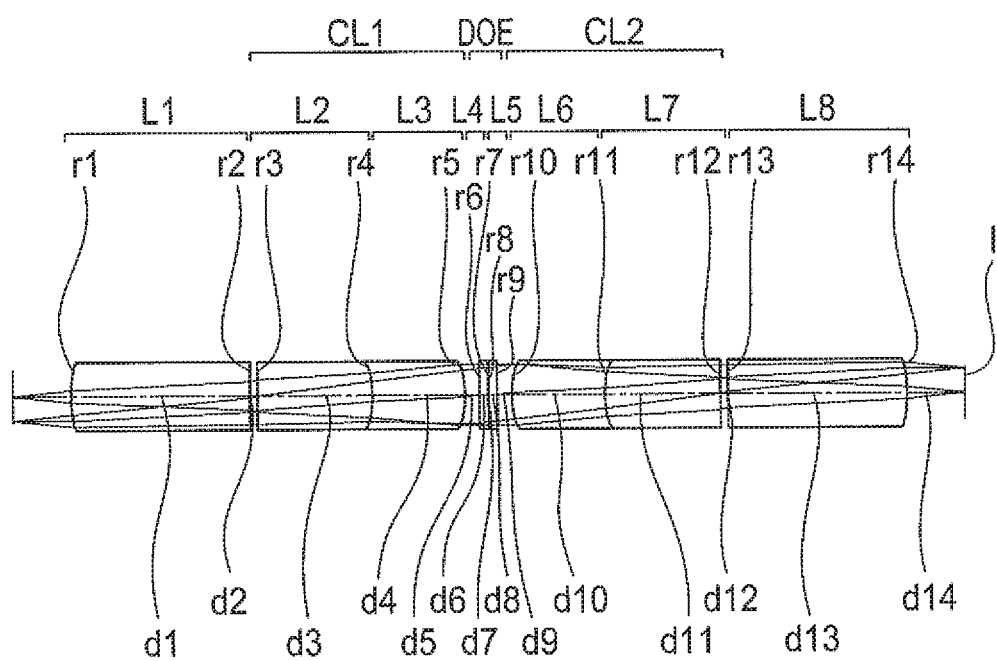
FIG. 3 is a lens cross-sectional view of a relay optical system of an example 2.
Figure 4:
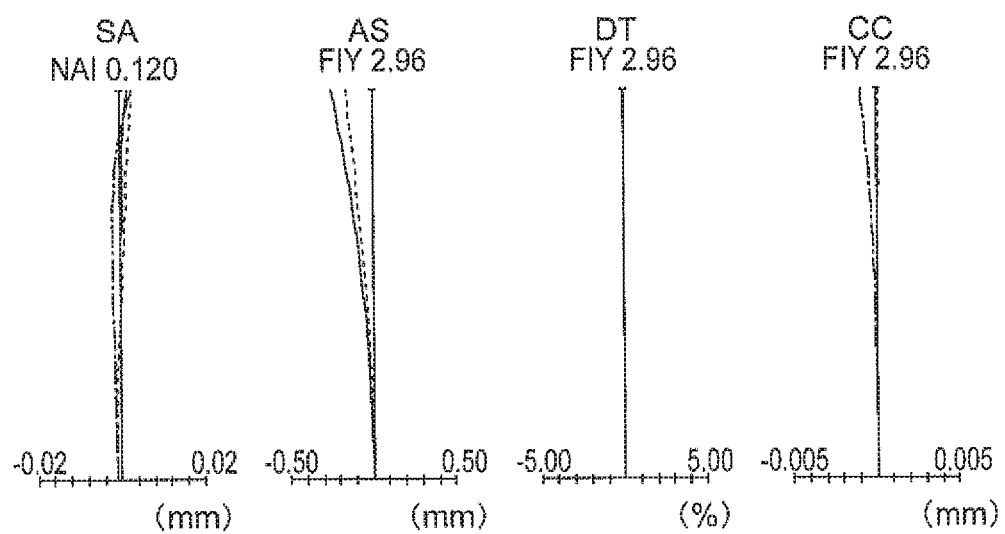
FIG. 4A, FIG. 4B, FIG. 4C, and FIG. 4D are aberration diagrams of the relay optical system of the example 2.
Figure 5:
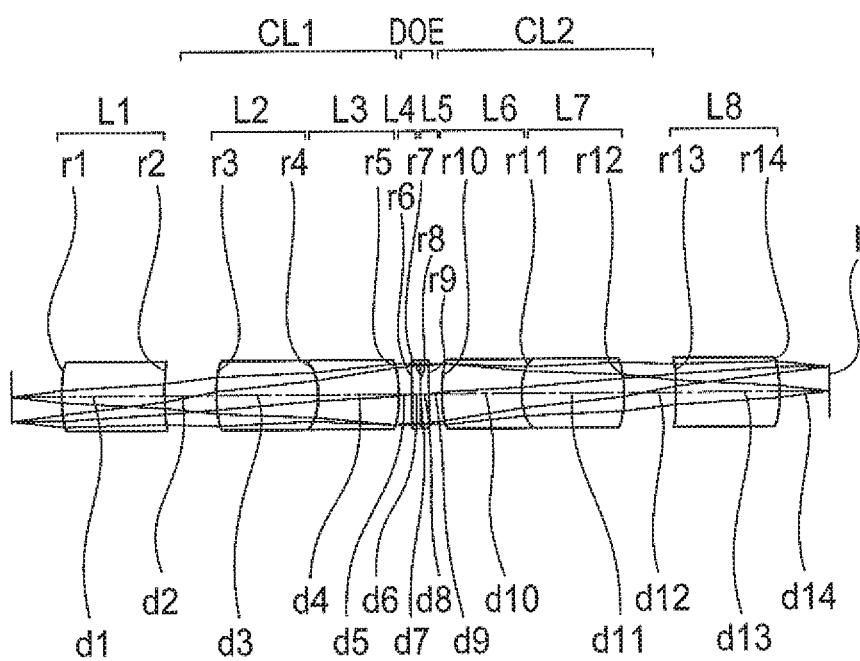
FIG. 5 is a lens cross-sectional view of a relay optical system of an example 3.
Figure 6:
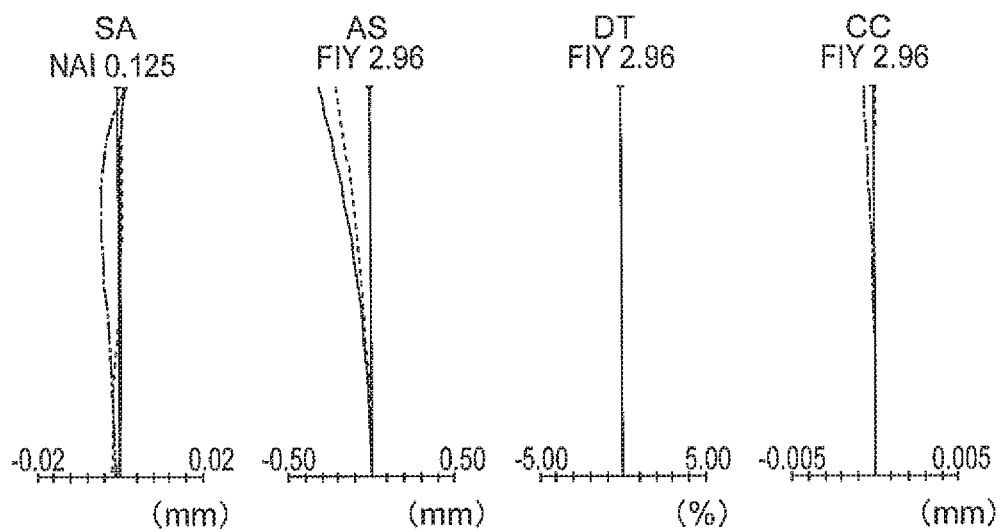
FIG. 6A, FIG. 6B, FIG. 6C, and FIG. 6D are aberration diagrams of the relay optical system of the example 3.
Figure 7:
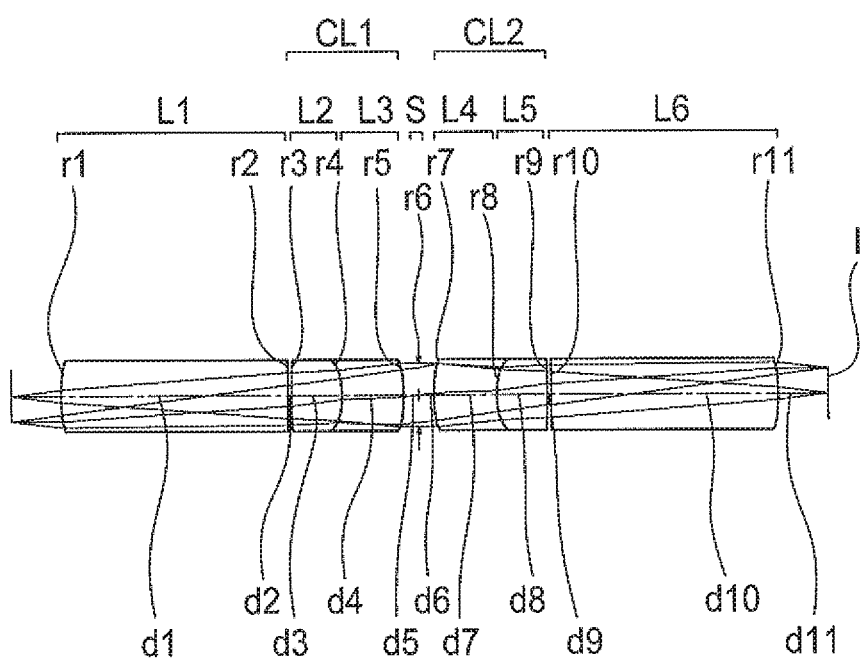
FIG. 7 is a lens cross-sectional view of a relay optical system of an example 4.
Figures 8A, 8B, 8C, 8D:
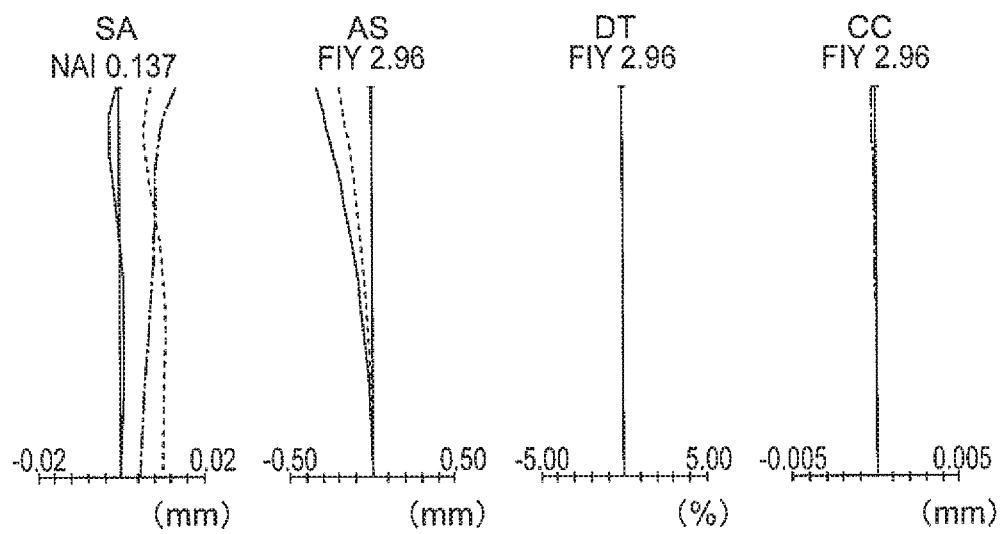
FIG. 8A, FIG. 8B, FIG. 8C, and FIG. 8D are aberration diagrams of the relay optical system of the example 4.
Figure 9:
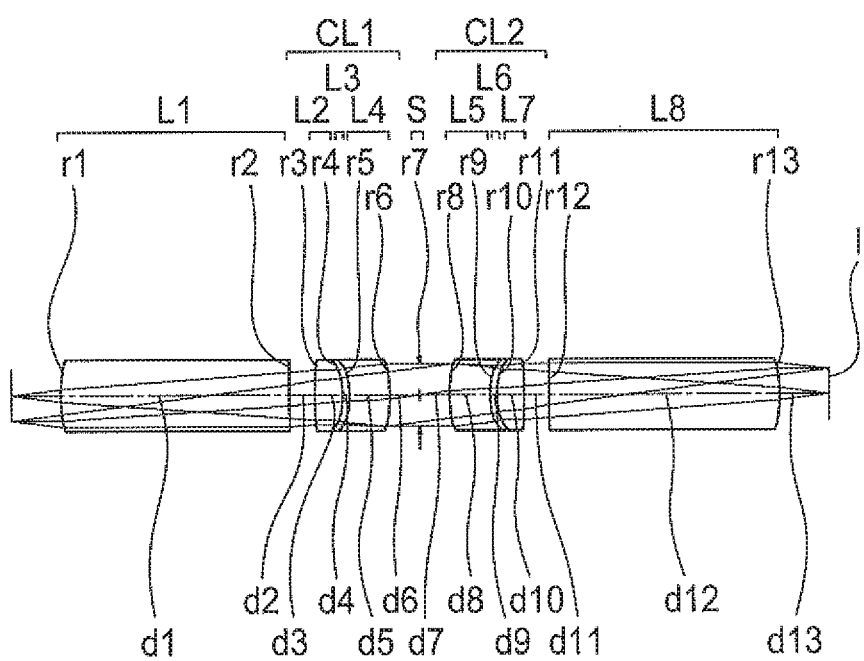
FIG. 9 is a lens cross-sectional view of a relay optical system of an example 5.
Figure 10:
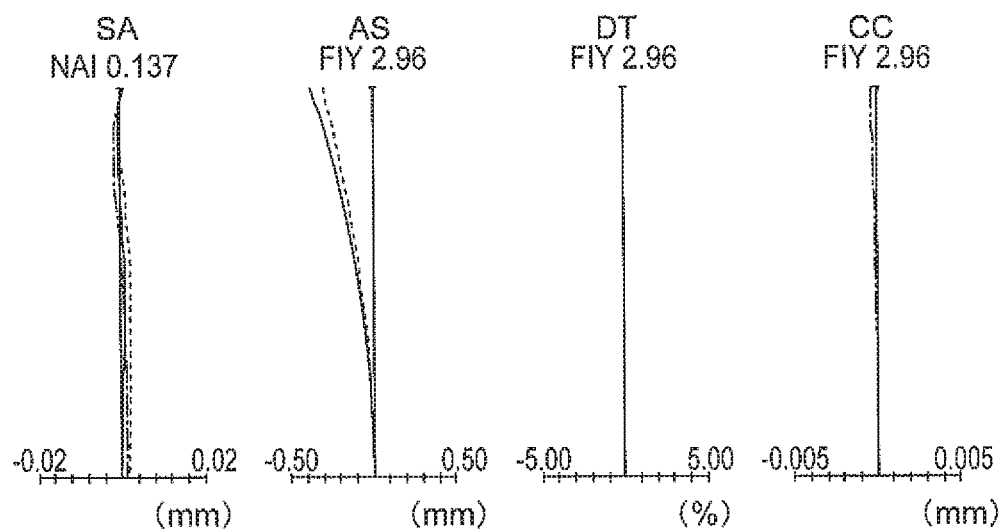
FIG. 10A, FIG. 10B, FIG. 10C, and FIG. 10D are aberration diagrams of the relay optical system of the example 5.
Figure 11:
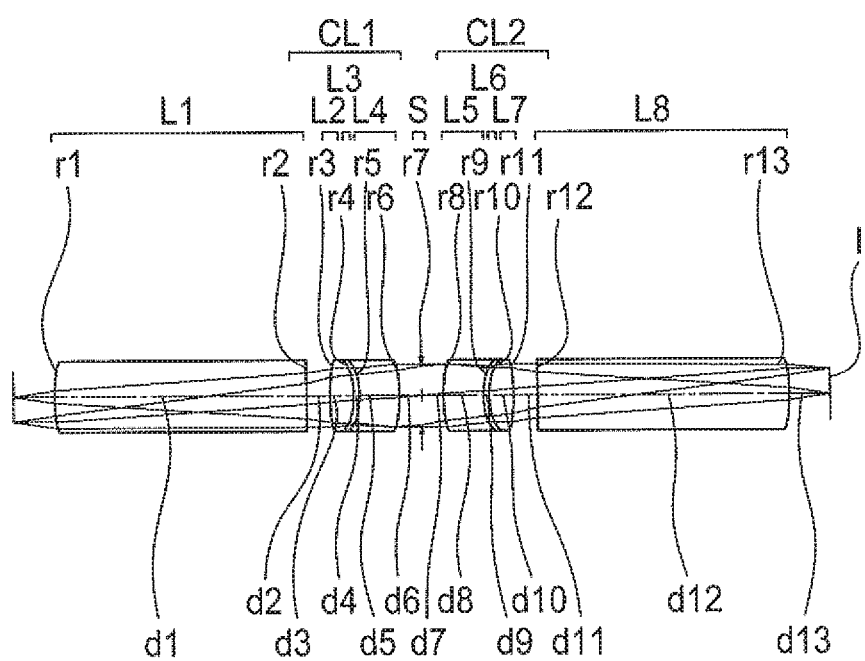
FIG. 11 is a lens cross-sectional view of a relay optical system of an example 6.
Figure 12:
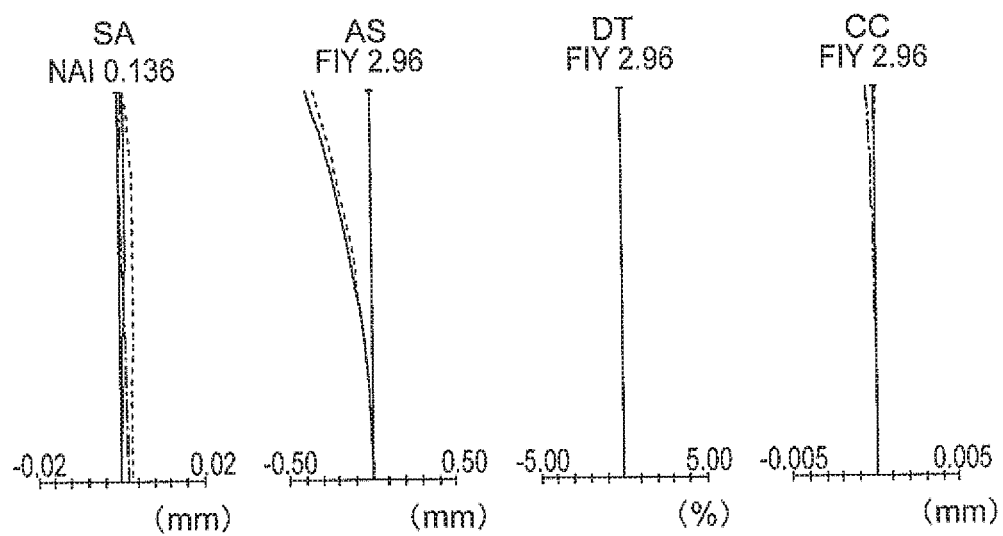
FIG. 12A, FIG. 12B, FIG. 12C, and FIG. 12D are aberration diagrams of the relay optical system of the example 6.

Reasons for and effects of adopting such arrangement for a relay optical system according to the present embodiment will be described below by using the accompanying diagrams. However, the present invention is not restricted to the relay optical system according to the present embodiment described below. Similar is true for an image relay unit, an optical system for rigid endoscope, and a rigid endoscope.

A relay optical system is used for relaying an image. The image relayed by a relay optical system is formed by an objective optical system. The objective optical system is disposed between an object and the relay optical system. A primary image of the object is formed by the objective optical system. The relay optical system relays the primary image, and forms an image (hereinafter, referred to as 'relay image'). An object side in the description below signifies a primary-image side, and an image side signifies a relay-image side. Moreover, an object plane signifies a plane at a position of the primary image, and an image plane signifies a plane at a position of the relay image.

The relay optical system of the present embodiment includes an object-side lens which is disposed nearest to an object, an image-side lens which is disposed nearest to an image, and a cemented lens having a positive refractive power, wherein the object-side lens has a positive refractive power and is disposed such that a convex surface is directed toward the object side, and the image-side lens has a positive refractive power and is disposed such that a convex surface is directed toward an image side, and a plurality of the cemented lenses is disposed between the object-side lens and the image-side lens, and the following conditional expression (1) is satisfied:

$$0.04 < Gce/Drel < 0.4 \tag{1}$$

where,

Gce denotes the smallest interval of intervals of adjacent cemented lenses, and

Drel denotes a distance from an object plane up to an image plane of the relay optical system.

For instance, let the relay optical system include in order from the object side, four lenses which are a lens A, a lens B, a lens C, and a lens D. Moreover, let an outer diameter of the relay optical system, be invariable.

In such arrangement, for making a numerical aperture of the relay optical system large, it is preferable to position a lens surface having a large refractive power close to the object plane or close to the image plane. With the above-mentioned arrangement, the lens A is disposed nearest to object and the lens D is positioned nearest to image. Therefore, with regard to the lens A, it is preferable to dispose such that a convex surface thereof is directed toward the object side, and for the lens D, it is preferable to dispose such that a convex surface thereof is directed toward the image side. By making such arrangement, it is possible to make the numerical aperture of the relay optical system large.

Moreover, for making the numerical aperture of the relay optical system large, a refractive power of each lens may be made large, and a combined refractive power of the two lenses may be made large. In a case of making the combined refractive power of the two lenses large, a combined refractive power of the lens A and the lens B, and a combined refractive power of the lens C and the lens D, are to be made large.

The combined refractive power of the lens A and the lens B will be described below. When a refractive power of the lens A is let to be $\phi_A$, a refractive power of the lens B is let to be $\phi_B$, and a distance between the lens A and the lens B is let to be $D_{AB}$, the combined refractive power $\phi_{AB}$ of the lens A and the lens B is expressed by the following formula.

$$\phi_{AB} = \phi_A + \phi_B - D_{AB}\phi_A\phi_B$$

As it is revealed from the abovementioned expression, by making the distance $D_{AB}$ small, it is possible to make the combined refractive power of $\phi_{AB}$ large. This indicates that for making the combine refractive power $\phi_{AB}$ large, the lens B is to be brought closer to the lens A.

Similar is true for the lens C and the lens C. For instance, by bringing the lens C closer to the lens D, it is possible to make the combined refractive power of the lens C and the lens D large.

When the lens B comes closer to the lens A and the lens C comes closer to the lens D, a distance between the lens B and the lens C widens. Therefore, by widening the distance between the lens B and the lens C, it is possible to make large the combined refractive power of the lens A and the lens B, and the combined refractive power of the lens C and the lens D.

When the refractive power of the lens C is let to be $\phi_C$ and the distance between the lens B and the lens C is let to be $D_{BC}$, the a combined refractive power $\phi_{BC}$ of the lens B and the lens C is expressed by the following formula.

$$\phi_{BC} = \phi_B + \phi_C - D_{BC}\phi_B\phi_C$$

Tentatively, in a case in which the combined refractive power $\phi_{BC}$ is let to be constant, by widening the distance $D_{BC}$, the refractive power $\phi_B$ of the lens B and the refractive power $\phi_C$ of the lens C become large. Widening the distance $D_{BC}$ refers to the lens B coming closer to the lens A. This signifies that the distance $D_{AB}$ becomes small in the formula for the combined refractive power $\phi_{AB}$. As the combined refractive power $\phi_{AB}$ becomes small, in the combined refractive power $\phi_{AB}$, $\phi_A$ becomes large and $D_{AB}$ becomes small. In such manner, by widening the distance $D_{BC}$, it is possible to make the combined refractive power $\phi_{AB}$ large.

Since the lens B and the lens C are positioned in the vicinity of a center of the optical system, a spherical aberration and a coma may be affected. By making the distance between the lens B and the lens C appropriate, it is possible to suppress an occurrence of the spherical aberration and an occurrence of the coma.

Each of the lens B and the lens C may be a cemented lens. In this case, by setting a distance between the adjacent cemented lenses to be appropriate, it is possible to make large the numerical aperture of the relay optical system while correcting aberrations favorably.

By making so as not to exceed arrangement such that an upper limit value of conditional expression (1), it is possible to suppress the distance between the adjacent cemented lenses from becoming excessively large. Accordingly, it is possible to suppress the refractive power of the cemented lens from becoming excessively large. As a result, it is possible to suppress an increase in the spherical aberration and an increase in the coma.

By making so as not to fall below a lower limit value of conditional expression (1), it is possible to suppress the distance between the adjacent cemented lenses from becoming excessively small. Accordingly, it is possible to suppress the refractive power of the cemented lens from becoming excessively small. As a result, it is possible to prevent the numerical aperture of the relay optical system from becoming excessively small.

In the calculation of a value of Drel and a value of Gce, an air conversion is not to be carried out.

It is preferable that the following conditional expression (1') be satisfied instead of conditional expression (1).

$$0.04 < Gce/Drel < 0.2 \quad (1')$$

It is more preferable that the following conditional expression (1") be satisfied instead of conditional expression (1).

$$0.04 < Gce/Drel < 0.15 \quad (1'')$$

In the relay optical system of the present embodiment, it is preferable that at least one cemented lens out of the plurality of cemented lenses include three lenses, and a medium of each of the three lenses be different, and one of the three lenses be a first lens, and in a rectangular coordinate system in which a horizontal axis is let to be $vd_{LA}$ and a vertical axis is let to be $\theta gF_{LA}$, when a straight line expressed by $\theta gF_{LA} = \alpha \times vd_{LA} + \beta_{LA}$ (where, $\alpha = -0.00163$) is set, $\theta gF_{LA}$ and $vd_{LA}$ of a medium of the first lens are included in an area determined by following conditional expression (2) and conditional expression (3):

$$0.64 < \beta_{LA} \quad (2)$$

$$vd_{LA} < 50 \quad (3)$$

where, $\theta gF_{LA}$ denotes a partial dispersion ratio $(ng_{LA} - nF_{LA})/(nF_{LA} - nC_{LA})$ of the medium of the first lens, and $vd_{LA}$ denotes Abbe number $(nd_{LA} - 1)/(nF_{LA} - nC_{LA})$ for the medium of the first lens, and here $nd_{LA}$, $nC_{LA}$, $nF_{LA}$, and $ng_{LA}$ denote refractive indices of the medium of the first lens for a d-line, a C-line, an F-line, and a g-line respectively.

In the relay optical system, it is necessary to relay the primary image without causing degradation of the primary image. In other words, it is necessary to make the relay image an image in which almost no degradation of the primary image has occurred. Therefore, it is important that no aberration is let to occur in the relay optical system as far as possible.

Aberrations that are susceptible to occur in a relay optical system are a chromatic aberration, the spherical aberration, and a curvature of field. As mentioned above, when the distance between the adjacent cemented lenses is made large, the refractive power of the cemented lens becomes large. Consequently, the chromatic aberration, the spherical aberration, and the curvature of field are susceptible to occur. Of these aberrations, it is preferable to correct favorably a longitudinal chromatic aberration in particular.

In the relay optical system of the present embodiment, at least one cemented lens of the plurality of cemented lenses includes three lenses. Moreover, the medium of each of the three lenses is different. Therefore, it is possible to carry out a correction of the chromatic aberration in which a difference in Abbe number is used. As a result, it is possible to carry out the correction of the chromatic aberration more favorably.

In the relay optical system of the present embodiment, $\theta gF_{LA}$ and $vd_{LA}$ of the medium of the first lens are included in the area determined by conditional expression (2) and conditional expression (3).

By making such arrangement, the medium of the first lens becomes a medium having an abnormal dispersion. The abnormal dispersion is a dispersion that differs from a dispersion of a normal glass lens. In a lens in which a medium having the abnormal dispersion is used, it is possible to generate a large refractive power for light of a short wavelength. Therefore, in the first lens, by making appropriate the refractive power for the light of the short wavelength, it is possible to correct the longitudinal chromatic aberration effectively.

By making so as not to fall below a lower limit value of conditional expression (2), it is possible to correct appropriately a secondary spectrum in the longitudinal chromatic aberration, or in other words, an aberration for the g-line that remains when achromatized at the F-line and the C-line. By making so as not to exceed an upper limit value of conditional expression (3), it is possible to correct appropriately a first-order chromatic aberration in the longitudinal chromatic aberration.

It is more preferable that the following conditional expression (2') be satisfied instead of conditional expression (2).

$$0.66 < \beta_{LA} < 0.9 \quad (2')$$

It is even more preferable that the following conditional expression (3') be satisfied instead of conditional expression (3).

$$3 < \nu d_{LA} < 50 \quad (3')$$

By making so as not to exceed an upper limit value of conditional expression (2'), it is possible to prevent a correction of the secondary spectrum in the longitudinal chromatic aberration from becoming excessive. By making so as not to fall below a lower limit value of conditional expression (3'), it is possible to prevent a correction of the first-order chromatic aberration in the longitudinal chromatic aberration from becoming excessive.

In the relay optical system of the present embodiment, it is preferable that the cemented lens which includes the first lens, include a second lens and an aspheric surface, and the following conditional expressions (4) and (5) be satisfied:

$$1.4 \leq nd_{LB} \leq 1.6 \quad (4)$$

$$70 \leq \nu d_{LB} \leq 100 \quad (5)$$

where, $nd_{LB}$, $nC_{LB}$, and $nF_{LB}$ denote refractive indices of the second lens for the d-line, the C-line, and the F-line respectively, and $\nu d_{LB}$ denotes Abbe number $(nd_{LB}-1)/(nF_{LB}-nC_{LB})$ for a medium of the second lens.

In the relay optical system of the present embodiment, it is preferable that at least one cemented lens out of the plurality of cemented lenses includes two lenses, and a medium of each of the two lenses is different, and one of the two lenses is a second lens, and the cemented lens which includes the second lens has the aspheric surface, and the following conditional expressions (4) and (5) are satisfied.

$$1.4 \leq nd_{LB} \leq 1.6 \quad (4)$$

$$70 \leq \nu d_{LB} \leq 100 \quad (5)$$

where, $nd_{LB}$, $nC_{LB}$, and $nF_{LB}$ denote refractive indices of the second lens for the d-line, the C-line, and the F-line respectively, and $\nu d_{LB}$ denotes Abbe number $(nd_{LB}-1)/(nF_{LB}-nC_{LB})$ for a medium of the second lens.

It is preferable that at least one cemented lens out of the plurality of cemented lenses include the second lens and the aspheric surface. The first lens may be or may not be included in this cemented lens.

As mentioned above, when the distance between the adjacent cemented lenses is made large, the refractive power of the cemented lens becomes large. Consequently, the spherical aberration, the coma, and the longitudinal chromatic aberration are susceptible to occur.

When the numerical aperture of the optical system is made large, the farther the position through which light passes, in a marginal area from an optical axis, the chromatic aberration is corrected excessively. Therefore, an arrangement is made such that the relay optical system includes at least one aspheric surface. By making such arrangement, it is possible to make the refractive power appropriate throughout the entire marginal area. As a result, even in a relay optical system with a large numerical aperture, it is possible to carry out the correction of the chromatic aberration in the marginal area favorably.

In this case, a medium of a low dispersion is used for the second lens. Consequently, according to a combination with the aspheric surface, it is possible to correct the chromatic aberration in the marginal area favorably.

In a case in which the first lens is included in the cemented lens, it is possible to let Abbe number for the medium of the second lens to differ substantially from Abbe number for the medium of the first lens. In other words, it is possible to make large a difference in Abbe number for the media of the two lenses. In this case, by the first lens and the second lens, it is possible to carry out the correction of the chromatic aberration in which the difference in Abbe number is used. Consequently, it is possible to carry out the correction of the chromatic aberration more favorably.

As mentioned above, the medium of the first lens has the abnormal dispersion. Therefore, by using the first lens, it is possible to correct the longitudinal chromatic aberration favorably. However, in the first lens, it is preferable to make appropriate the refractive power for the light of the short wavelength according to a size of the numerical aperture of the optical system.

It is possible to make appropriate the refractive power for the light of the short wavelength by using the aspheric surface. Therefore, it is preferable to provide the aspheric surface to the first lens. By making such arrangement, even in a relay optical system with a large numerical aperture, it is possible to carry out the correction of the chromatic aberration in the marginal area more favorably.

In the case in which the first lens is included in the cemented lens, it is preferable to provide the aspheric surface to the first lens. In a case in which the first lens is not included in the cemented lens, it is preferable to provide the aspheric surface to the second lens.

In a case of falling below a lower limit value of conditional expression (4), for securing the required refractive power for the cemented lens, a radius of curvature of a lens surface has to be made small. Consequently, the spherical aberration is degraded. In a case of exceeding an upper limit value of conditional expression (4), a glass material that can be used for lens does not exist.

In a case of falling below a lower limit value of conditional expression (5), the correction of the chromatic aberration becomes inadequate. In a case of exceeding an upper limit value of conditional expression (5), a glass material that can be used for lens does not exist.

The aspheric surface may be provided to a surface on one side of the lens or to surfaces on both sides of the lens. Moreover, the number of lenses to be provided with the aspheric surface is not restricted to one.

It is more preferable that the following conditional expression (4') be satisfied instead of conditional expression (4).

$$1.4 < nd_{LB} < 1.55 \quad (4')$$

It is even more preferable that the following conditional expression (5') be satisfied instead of conditional expression (5).

$$60 < \nu d_{LB} < 100 \quad (5')$$

In the relay optical system of the present embodiment, it is preferable that a diffractive optical element be disposed between the object-side lens and the image-side lens.

As mentioned above, when the distance between the adjacent cemented lenses is made large, the refractive power of the cemented lens becomes large. Consequently, the spherical aberration, the comma aberration, and the longitudinal chromatic aberration are susceptible to occur. Of these aberrations, it is preferable to correct favorably the longitudinal chromatic aberration in particular.

Abbe number for the diffractive optical element in a visible range is −3.453. Thus, the diffractive optical element has an extremely strong negative dispersion characteristic. Whereas, Abbe number for a normal glass material is approximately 20 to 95. Accordingly, it is evident that the diffractive optical element has an extremely strong dispersion characteristic opposite to that of the normal glass material. Moreover, by similar calculation, it is revealed that the diffractive optical element has an abnormal dispersion.

In the relay optical system of the present embodiment, the diffractive optical element is disposed between the object-side lens and the image-side lens. By using the diffractive optical element, it is possible to carry out an aberration correction in which the dispersion characteristic opposite to that of a glass material is used. In other words, it is possible to cancel the longitudinal chromatic aberration occurred in the cemented lens, by the diffractive optical element.

However, in the normal glass or resin, dispersion is non-linear with respect to a wavelength. Whereas in the diffractive optical element, the dispersion is linear with respect to the wavelength. Consequently, in a case in which the number of lenses in the optical system is small, only by using the diffractive optical element alone, the chromatic aberration is not corrected thoroughly in a wavelength band of white light.

The relay optical system of the present embodiment, as a dioptric system, includes the object-side lens, the plurality of cemented lenses, and the image-side lens. By using a plurality of lenses in such dioptric system, it is possible to bring a dispersion in the overall dioptric system closer to linear. As a result, it is possible to carry out effectively the correction of the chromatic aberration by the diffractive optical element.

Moreover, by disposing the diffractive optical element between the object-side lens and the image-side lens, it is possible to make a light ray incident on the diffractive optical element to be almost perpendicular. As a result, it is possible to improve a diffraction efficiency.

In the relay optical system of the present embodiment, it is preferable that the following conditional expression (6) be satisfied:

$$0.05 < Dcd/Drel < 0.30 \qquad (6)$$

where,

Dcd denotes a distance from a cemented surface up to a diffractive surface of the diffractive optical element, and Drel denotes a distance from the object plane up to the image plane of the relay optical system, and here the cemented surface is a cemented surface of the cemented lens which is positioned nearest to the diffractive optical element.

In the correction of the chromatic aberration, it is preferable to balance a negative dispersion by the diffractive optical element and a positive dispersion by the cemented lens. When a distance from a cemented surface up to the diffractive surface of the diffractive optical element is not appropriate, the balance of the two dispersions is disrupted. Consequently, an appropriate correction of the longitudinal chromatic aberration is not possible.

By making so as not to exceed an upper limit value of conditional expression (6), it is possible to maintain a distance between the cemented surface and the diffractive optical element to be adequate. Consequently, it is possible to prevent the refractive power of the cemented surface from becoming excessively large. As a result, it is possible to prevent the correction of the longitudinal chromatic aberration from becoming inadequate.

By making so as not to fall below a lower limit value of conditional expression (6), it is possible to prevent the refractive power of the cemented surface from becoming excessively small. As a result, it is possible to prevent the longitudinal chromatic aberration from being excessively.

In the calculation of a value of Dcd and the value of Drel, an air conversion is not to be carried out.

It is more preferable that the following conditional expression (6') be satisfied instead of conditional expression (6).

$$0.06 < Dcd/Drel < 0.20 \qquad (6')$$

It is even more preferable that the following conditional expression (6") be satisfied instead of conditional expression (6)

$$0.07 < Dcd/Drel < 0.18 \qquad (6")$$

In the relay optical system of the present embodiment, it is preferable that the following conditional expression (7) be satisfied:

$$0.2 < (OBH+IH)/\Phi doe < 1.2 \qquad (7)$$

where, $\Phi$doe denotes a light-ray effective diameter of the diffractive optical element, OBH denotes the maximum object height, and IH denotes the maximum image height.

In relay optical systems, there are a relay optical system in which an image height of the primary image is high, a relay optical system in which an image height of the relay image is high, and a relay optical system in which both the image height of the primary image and the image height of the relay image are high. In such relay optical systems in which the image height is high, a height of a light ray that passes through the relay optical system also becomes high. When a virtual plane orthogonal to an optical axis is assumed to be positioned at a center of the relay optical system, an angle of incidence on the virtual plane tends to be large.

In the relay optical system of the present embodiment, the diffractive optical element is disposed near the center of the relay optical system. When an angle of incidence on the diffractive optical element becomes large, the diffraction efficiency is degraded with the image height becoming higher. In this case, brightness in a periphery of an image is lowered with respect to a brightness at a center of the image.

Therefore, by using the cemented lens and the diffractive optical element and satisfying conditional expression (7), it is possible to correct the chromatic aberration in an optical axial direction favorably. The light-ray effective diameter is a diameter in which the maximum light-ray height among the light-ray heights of light rays passing through the diffractive optical element is doubled.

By making so as not to exceed an upper limit value of conditional expression (7), it is possible to suppress the degradation of the diffraction efficiency of the diffractive optical element at a position at which the light-ray height is the maximum. As a result, even in a case in which an object height or an image height is high, it is possible to prevent degradation of the brightness in the periphery of the image.

By making so as not to fall below a lower limit value of conditional expression (7), it is possible to suppress a size in a radial direction of the relay optical system from becoming large while maintaining high the image height of the primary image and the image height of the relay image.

It is more preferable that the following conditional expression (7') be satisfied instead of conditional expression (7).

$$0.4<(OBH+IH)/\Phi doe<1.1 \tag{7'}$$

It is even more preferable that the following conditional expression (7") be satisfied instead of conditional expression (7).

$$0.6<(OBH+IH)/\Phi doe<1.0 \tag{7"}$$

In the relay optical system of the present embodiment, it is preferable that the following conditional expression (8) be satisfied:

$$0.3<FLdoe/(\Phi doe\times100)<15 \tag{8}$$

where,

FLdoe denotes a focal length of the diffractive optical element, and

Φdoe denotes the light-ray effective diameter of the diffractive optical element.

In the relay optical system of the present embodiment, the chromatic aberration remained in the dioptric system is cancelled by the chromatic aberration that occurs in the diffractive optical element, by using an effect based on the negative dispersion characteristic of the diffractive optical element. Accordingly, a favorable imaging performance is achieved.

In assembling the optical system, lenses are housed in holding frames one after another. In a case in which a manufacturing error such as decentering occurs, in a state of the optical system assembled initially, the chromatic aberration remains without being cancelled. In this case, there is a degradation of imaging performance. To prevent the degradation of imaging performance, decentering adjustment is carried out in a manufacturing process, and an arrangement is made such that the chromatic aberration is cancelled.

In a case in which either the focal length of the diffractive optical element becomes excessively large or the light-ray effective diameter becomes excessively small, the number of ring-shaped zones of a diffraction grating becomes small. For instance, when there is a manufacturing error in one ring-shaped zone, in a case in which the number of ring-shaped zone is small, an effect of the manufacturing error becomes large. In this case, an adjustment work in the decentering adjustment becomes complicated. Whereas, in a case in which the number of ring-shaped zones is large, the effect of manufacturing error is small. In this case, the adjustment work in the decentering adjustment becomes easy.

In such manner, when the number of ring-shaped zones of the diffraction grating becomes small, a redundancy of a diffraction effect at a diffractive surface is lowered. As the redundancy of the diffraction effect is lowered, for instance, in a case of cancelling the chromatic aberration, the adjustment work in the decentering adjustment becomes complicated.

When the relay optical system includes a plurality of diffractive optical elements, one diffractive optical element of the plurality of diffractive optical elements may satisfy conditional expression (8).

By making so as not to exceed an upper limit value of conditional expression (8), it is possible to prevent the number of ring-shaped zones of the diffractive optical element from becoming excessively small. By making so as not to fall below a lower limit value of conditional expression (8), a necessity of the decentering arrangement etc. is reduced, and it is possible to reduce degradation of imaging performance while simplifying the manufacturing process.

It is more preferable that the following conditional expression (8') be satisfied instead of conditional expression (8).

$$0.5<FLdoe/(\Phi doe\times100)<10 \tag{8'}$$

It is even more preferable that the following conditional expression (8") be satisfied instead of conditional expression (8).

$$1.8<FLdoe/(\Phi doe\times100)<8 \tag{8"}$$

In the relay optical system of the present embodiment, it is preferable that the plurality of cemented lenses be disposed in an optical path of the relay optical system, which is formed by an object-side optical path and an image-side optical path, and a lens surface positioned nearest to the image in the object-side optical path be a surface which is convex toward the image side, and a lens surface positioned nearest to the object in the image-side optical path be a surface which is convex toward the object side.

When a numerical aperture of the relay optical system is made large, an amount of occurrence of the spherical aberration and an amount of occurrence of the coma become large. By making the abovementioned arrangement, it is possible to suppress an increase in the amount of occurrence of the spherical aberration and an increase in the amount of occurrence of the coma.

It is possible to divide an optical path of a relay optical system into the object-side optical path and the image-side optical path with a center of the relay optical system as a boundary, for example. A plurality of cemented lenses is either to be disposed in at least one of the object-side optical path and the image-side optical path or to be disposed to spread over both the optical paths.

By the cemented lens being disposed in each of the object-side optical path and the image side optical path, it is possible to correct various aberrations favorably. Here, a cemented lens positioned nearest to the image in the object-side optical path is disposed such that a lens surface on the image side is convex toward the image side. Moreover, a cemented lens positioned nearest to the object in the image-side optical path is disposed such that a lens surface on the object side is convex toward the object side. By making such arrangement, it becomes a state in which two convex surfaces are face-to-face at the center of the relay optical system. As a result, it is possible to suppress an occurrence of the spherical aberration and an occurrence of the coma.

In the relay optical system of the present embodiment, it is preferable that the following conditional expression (9) be satisfied:

$$1<FLce/Gce<20 \tag{9}$$

where,

FLce denotes an average value of focal lengths of the adjacent cemented lenses, and Gce denotes the smallest interval of intervals of adjacent cemented lenses.

In a relay optical system, it is preferable to make the numerical aperture large while making an outer diameter small. For this, it is significant to make the focal lengths of the two cemented lenses small while widening the distance between the two adjacent cemented lenses. It is preferable not to let the aberration to be degraded at the time of making the focal lengths of the cemented lenses small.

By making so as not to exceed an upper limit value of conditional expression (9), it is possible to prevent the numerical aperture of the relay optical system from becoming small. By making so as not to fall below a lower limit value of conditional expression (9), it is possible to prevent the focal lengths of the cemented lenses from becoming excessively small. As a result, it is possible to suppress a degradation of the spherical aberration and a degradation of the coma.

It is more preferable that the following conditional expression (9') be satisfied instead of conditional expression (9)

$$2<FLce/Gce<15 \quad (9')$$

It is even more preferable that the following conditional expression (9") be satisfied instead of conditional expression (9).

$$3<FLce/Gce<10 \quad (9'')$$

In the relay optical system of the present embodiment, it is preferable that the following conditional expressions (A) and (B) be satisfied.

$$0.09<NA<0.3 \quad (A)$$

$$50<|FLrel| \quad (B)$$

where,

NA denotes the numerical aperture of the relay optical system, and

FLrel denotes a focal length of the relay optical system.

By satisfying conditional expressions (A) and (B), it is possible to realize a relay optical system with a short overall length which is capable of forming a high-resolution relay image.

In the relay optical system of the present embodiment, it is preferable that the diffractive optical element be disposed between the two cemented lenses.

By making such arrangement, it is possible to make a light ray incident on the diffractive optical element almost perpendicular to a surface of incidence of the diffractive optical element. As a result, it is possible to improve the diffraction efficiency. It is more preferable that the diffractive optical element be disposed between the cemented lens positioned nearest to the image in the object-side optical path and the cemented lens positioned nearest to the object in the image-side optical path.

In the relay optical system of the present embodiment, it is preferable that the diffractive optical element include a first optical member and a second optical member, and the following conditional expressions (C), (D), (E), and (F) be satisfied.

$$1.50 \leq nd1 \leq 1.70 \quad (C)$$

$$15 \leq vd1 \leq 35 \quad (D)$$

$$1.60 \leq nd2 \leq 1.80 \quad (E)$$

$$35 \leq vd2 \leq 60 \quad (F)$$

where, nd1, nC1, and nF1 denote refractive indices of a material of the first optical member for the d-line, the C-line, and the F-line, vd1 is Abbe number (nd1−1)/(nF1−nC1) for the material of the first optical member, nd2, nC2, and nF2 denote refractive indices of a material of the second optical member for the d-line, the C-line, and the F-line, and vd2 denotes Abbe number (nd2−1)/(nF2−nC2) for the material of the second optical member.

In a case in which the focal length of the diffractive optical element is long, a blaze angle of the diffractive surface tends to be small. In this case, it is difficult to carry out easily the processing of the diffractive surface. By satisfying conditional expressions (C), (D), (E), and (F), it is possible to make a difference in refractive indices of the two optical members adequately small. In this case, it is possible to make a shape of the diffractive surface a shape that can be processed. As a result, it is possible to carry out the processing of the diffractive surface easily.

An image relay unit of the present embodiment includes a plurality of relay optical systems, and at least one relay optical system of the plurality of relay optical systems is the relay optical system of the present embodiment.

As mentioned above, in the relay optical system of the present embodiment, the chromatic aberration is corrected favorably. Therefore, by using at least one relay optical system of the present embodiment in the image relay unit, it is possible to realize an image relay unit in which the chromatic aberration is small. By using a plurality of relay optical systems of the present embodiment, it is possible to realize an image relay unit in which the chromatic aberration is further smaller.

For forming a relay image with high resolution, it is desirable to make large the numerical aperture of the relay optical system. However, when the numerical aperture of the relay optical system is made large, the chromatic aberration is susceptible to occur.

Moreover, it is possible to use the image relay unit in an optical system for rigid endoscope. As mentioned above, in a case of making appropriate the overall length of the optical system for rigid endoscope by adjusting the number of relay optical systems, it is preferable that the overall length of the relay optical system be short. When the overall length of the relay optical system is made short, the numerical aperture becomes large. Even in this case, the chromatic aberration is susceptible to occur.

In the relay optical system of the present embodiment, the chromatic aberration is corrected favorably. Therefore, even when the numerical aperture is made large, it is possible to suppress an increase in the chromatic aberration. Therefore, by using the relay optical system of the present embodiment in the image relay unit, it is possible to realize an image relay unit in which the numerical aperture is large and the chromatic aberration is corrected favorably.

An image relay unit of the present embodiment includes a predetermined relay optical system, and a relay optical system consisting of lenses, wherein the number of the relay optical systems consisting of lenses is larger than the number of the predetermined relay optical systems, and the predetermined relay optical system is the relay optical system of the present embodiment, and the following conditional expression (10) is satisfied:

$$0.05<NAI \times FLdoe/Dreall<1.5 \quad (10)$$

where,

NAI denotes an image-side numerical aperture of the relay optical system,

FLdoe denotes a focal length of the diffractive optical element, and

Dreall denotes a distance from the object plane up to an image plane of the image relay unit.

The image relay unit includes the plurality of relay optical systems. Therefore, a plurality of relay images is formed. As mentioned above, an object plane of the image relay unit is a plane at the position of the primary image. An image plane of the image relay unit is a plane at the position of the relay image formed last of all of the plurality of relay images.

The diffractive optical element has a high correction performance for the chromatic aberration. Therefore, by the predetermined relay unit being equipped with the diffractive optical element, it is possible to correct the chromatic aberration favorably by the predetermined relay optical system alone. In a rigid endoscope, an image relay unit equipped with a plurality of relay optical systems is used. In this case, the image relay unit may be formed by the predetermined relay optical system only. However, the image relay unit may include the predetermined relay optical system and a relay optical system consisting of lenses.

In the latter case, in the relay optical system consisting of lenses, it is possible to tolerate an occurrence of the chromatic aberration to certain extent. As mentioned above, the diffractive optical element has the high correction performance for the chromatic aberration. Therefore, it is possible to correct the chromatic aberration occurred in the relay optical system consisting of lenses, by the predetermined relay optical system. The number of relay optical systems consisting of lenses may be more than the number of the predetermined relay optical systems. Even in such case, it is possible to correct the chromatic aberration in the overall image relay unit favorably.

However, when an amount of the chromatic aberration which is to be corrected by the diffractive optical element is made large, a focal length of the predetermined relay optical system becomes small. In this case, when there is a manufacturing error such as decentering, in an initially assembled state of the optical system, the chromatic aberration occurred in the relay optical system consisting of lenses cannot be cancelled in the predetermined relay optical system. Consequently, when no decentering adjustment is carried out, an imaging performance of the image relay unit is degraded. In a case of a large numerical aperture, the degradation of imaging performance appears remarkably.

By making so as not to exceed an upper limit value of conditional expression (10), it is possible to prevent the number of ring-shaped zones of the diffractive optical element from becoming excessively small. In this case, since it is possible to improve the redundancy of the diffraction effect at the diffractive surface, it is possible to generate a necessary amount of the chromatic aberration. Therefore, in a case of cancelling the chromatic aberration, it is possible to carry out easily the adjustment work of the decentering adjustment. The necessary amount of the chromatic aberration refers to an amount of chromatic aberration that is necessary for cancelling the chromatic aberration occurred in the relay optical system consisting of lenses.

By making so as not to fall below a lower limit value of conditional expression (10), the necessity of the decentering adjustment etc. is reduced, and it is possible to reduce the degradation of imaging performance while simplifying the manufacturing process.

It is more preferable that the following conditional expression (10') be satisfied instead of conditional expression (10).

$$0.15 < NAI \times FLdoe/Dreall < 1.0 \tag{10'}$$

It is even more preferable that the following conditional expression (10″) be satisfied instead of conditional expression (10).

$$0.20 < NAI \times FLdoe/Dreall < 0.7 \tag{10″}$$

An optical system for rigid endoscope of the present embodiment includes an objective optical system and an image relay unit which is disposed on an image side of the objective optical system, wherein the image relay unit is the image relay unit of the present embodiment.

By using the image relay unit of the present embodiment, it is possible to realize an optical system for rigid endoscope in which the chromatic aberration is corrected favorably and the numerical aperture is large.

The optical system for rigid endoscope of the present embodiment includes an eyepiece optical system which is disposed on an image side of the image relay unit.

By making such arrangement, it is possible to observe a bright optical image in which the chromatic aberration is corrected favorably.

A rigid endoscope of the present embodiment includes the optical system for rigid endoscope of the present embodiment, and an image pickup element which captures an image formed by the image relay unit.

When the optical system for rigid endoscope of the present embodiment is used, an optical image is formed by the image relay unit of the present embodiment. This optical image is bright, and the chromatic aberration is corrected favorably in this optical image. Therefore, by capturing this optical image by the image pickup element, it is possible to acquire a bright image with small chromatic aberration.

The rigid endoscope of the present embodiment includes an illuminating unit for illuminating an object to be observed.

By making such arrangement, it is possible to carry out an observation of a bright optical image with the small chromatic aberration and an acquisition of a bright image with the small chromatic aberration.

Examples of the relay optical system, the image relay unit, the optical system for rigid endoscope, and the rigid endoscope will be described below by referring to the accompanying diagrams. However, the present invention is not restricted to the examples described below.

Examples of the relay optical system will be described below. FIG. 1, FIG. 3, FIG. 5, FIG. 7, FIG. 9, and FIG. 11 are lens cross-sectional views of the relay optical systems of the examples.

Aberration diagrams of the examples will be described below.

FIG. 2A, FIG. 4A, FIG. 6A, FIG. 8A, FIG. 10A, and FIG. 12A show a spherical aberration (SA).

FIG. 2B, FIG. 4B, FIG. 6B, FIG. 8B, FIG. 10B, and FIG. 12B show an astigmatism (AS).

FIG. 2C, FIG. 4C, FIG. 6C, FIG. 8C, FIG. 10C, and FIG. 12C show a distortion (DT).

FIG. 2D, FIG. 4D, FIG. 6D, FIG. 8D, FIG. 10D, and FIG. 12D show a chromatic aberration of magnification (CC).

In each example, an aperture stop S is disposed in the relay optical system. However, the aperture stop S may not have been disposed in the relay optical system provided that it is possible to determine a light-beam diameter even without using the aperture stop S.

A relay optical system of an example 1 includes in order from an object side, a positive meniscus lens L1 having a convex surface directed toward the object side, a cemented lens CL1 having a positive refractive power, a diffractive optical element DOE, a cemented lens CL2 having a positive refractive power, and a positive meniscus lens L8 having a convex surface directed toward an image side.

The cemented lens CL1 includes a biconvex positive lens L2 and a negative meniscus lens L3 having a convex surface directed toward the image side.

The diffractive optical element DOE includes a first plane parallel plate L4 and a second plane parallel plate L5. The first plane parallel plate L4 and the second plane parallel plate L5 are cemented, and a diffractive surface is formed on a cemented surface.

The cemented lens CL2 includes a negative meniscus lens L6 having a convex surface directed toward the object side, and a biconvex positive lens L7.

In the relay optical system of the example 1, the positive meniscus lens L1 and the positive meniscus lens L8 are symmetrical. Moreover, the cemented lens CL1 and the cemented lens CL2 are symmetrical. In the relay optical system of the example 1, a symmetry plane exists at a cemented surface of the diffractive optical element DOE.

A relay optical system of an example 2 includes in order from an object side, a biconvex positive lens L1, a cemented lens CL1 having a positive refractive power, a diffractive optical element DOE, a cemented lens CL2 having a positive refractive power, and a biconvex positive lens L8.

The cemented lens CL1 includes a positive meniscus lens L2 having a convex surface directed toward an image side and a negative meniscus lens L3 having a convex surface directed toward the image side.

The diffractive optical element DOE includes a first plane parallel plate L4 and a second plane parallel plate L5. The first plane parallel plate L4 and the second plane parallel plate L5 are cemented, and a diffractive surface is formed on a cemented surface.

The cemented lens CL2 includes a negative meniscus lens L6 having a convex surface directed toward the object side and a positive meniscus lens L7 having a convex surface directed toward the object side.

In the relay optical system of the example 2, the biconvex positive lens L1 and the biconvex positive lens L8 are symmetrical. Moreover, the cemented lens CL1 and the cemented lens CL2 are symmetrical. In the relay optical system of the example 2, a symmetry plane exists at the cemented surface of the diffractive optical element DOE.

A relay optical system of an example 3 includes in order from an object side, a positive meniscus lens L1 having a convex surface directed toward the object side, a cemented lens CL1 having a positive refractive power, a diffractive optical element DOE, a cemented lens CL2 having a positive refractive power, and a positive meniscus lens L8 having a convex surface directed toward an image side.

The cemented lens CL1 includes a biconvex positive lens L2 and a negative meniscus lens L3 having a convex surface directed toward the image side.

The diffractive optical element DOE includes a first plane parallel plate L4 and a second plane parallel plate L5. The first plane parallel plate L4 and the second plane parallel plate L5 are cemented, and a diffractive surface is formed on a cemented surface.

The cemented lens CL2 includes a negative meniscus lens L6 having a convex surface directed toward the object side and a biconvex positive lens L7.

In the relay optical system of the example 3, the positive meniscus lens L1 and the positive meniscus lens L8 are symmetrical. Moreover, the cemented lens CL1 and the cemented lens CL2 are symmetrical. In the relay optical system of the example 3, a symmetry plane exists at the cemented surface of the diffractive optical element DOE.

A relay optical system of an example 4 includes in order from an object side, a planoconvex positive lens L1, a cemented lens CL1 having a positive refractive power, a cemented lens CL2 having a positive refractive power, and a planoconvex positive lens L6. An aperture stop S is disposed between the cemented lens CL1 and the cemented lens CL2.

The cemented lens CL1 includes a biconvex positive lens L2 and a negative meniscus lens L3 having a convex surface directed toward an image side.

The cemented lens CL2 includes a negative meniscus lens L4 having a convex surface directed toward the object side and a biconvex positive lens L5.

The biconvex positive lens L2 is the second lens and the biconvex positive lens L5 is the second lens.

In the relay optical system of the example 4, the planoconvex positive lens L1 and the planoconvex positive lens L8 are symmetrical with respect to the aperture stop S. Moreover, the cemented lens CL1 and the cemented lens CL2 are symmetrical with respect to the aperture stop S. In the relay optical system of the example 4, a symmetry plane exists at a position of the aperture stop S.

An aspheric surface is provided to a total of two surfaces which are an object-side surface of the biconvex positive lens L2 and an image-side surface of the biconvex positive lens L5. A relay optical system of an example 5 includes in order from an object side, a planoconvex positive lens L1, a cemented lens CL1 having a positive refractive power, a cemented lens CL2 having a positive refractive power, and a planoconvex positive lens L8. An aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side.

The cemented lens CL2 includes a negative meniscus lens L5 having a convex surface directed toward the object side, a positive meniscus lens L6 having a convex surface directed toward the object side, and a biconvex positive lens L7.

The positive meniscus lens L3 is the first lens and the positive meniscus lens L6 is the first lens. The biconvex positive lens L2 is the second lens and the biconvex positive lens L7 is the second lens.

In the relay optical system of the example 5, the planoconvex positive lens L1 and the planoconvex positive lens L8 are symmetrical with respect to the aperture stop S. Moreover, the cemented lens CL1 and the cemented lens CL2 are symmetrical with respect to the aperture stop S. In the relay optical system of the example 5, a symmetry plane exists at a position of the aperture stop S.

An aspheric surface is provided to a total of two surfaces which are an image-side surface of the positive meniscus lens L3 and an object-side surface of the positive meniscus lens L6.

A relay optical system of an example 6 includes in order from an object side, a planoconvex positive lens L1, a cemented lens CL1 having a positive refractive power, cemented lens CL2 having a positive refractive power, and a planoconvex positive lens L8. An aperture stop S is disposed between the cemented lens CL1 and the cemented lens CL2.

The cemented lens CL1 includes a biconvex positive lens L2, a positive meniscus lens L3 having a convex surface directed toward an image side, and a negative meniscus lens L4 having a convex surface directed toward the image side.

The cemented lens CL2 includes a negative meniscus lens L5 having a convex surface directed toward the object side, a positive meniscus lens L6 having a convex surface directed toward the object side, and a biconvex positive lens L7.

The positive meniscus lens L3 is the first lens and the positive meniscus lens L6 is the first lens. The biconvex positive lens L2 is the second lens and the biconvex positive lens L7 is the second lens.

In the relay optical system of the example 6, the planoconvex positive lens l1 and the planoconvex positive lens L8 are symmetrical with respect to the aperture stop S. Moreover, the cemented lens CL1 and the cemented lens CL2 are symmetrical with respect to the aperture stop S. In the relay optical system of the example 6, a symmetry plane exists at a position of the aperture stop S.

An aspheric surface is provided to a total of two surfaces which are an image-side surface of the positive meniscus lens L3 and an object-side surface of the positive meniscus lens L6.

Figure 13:
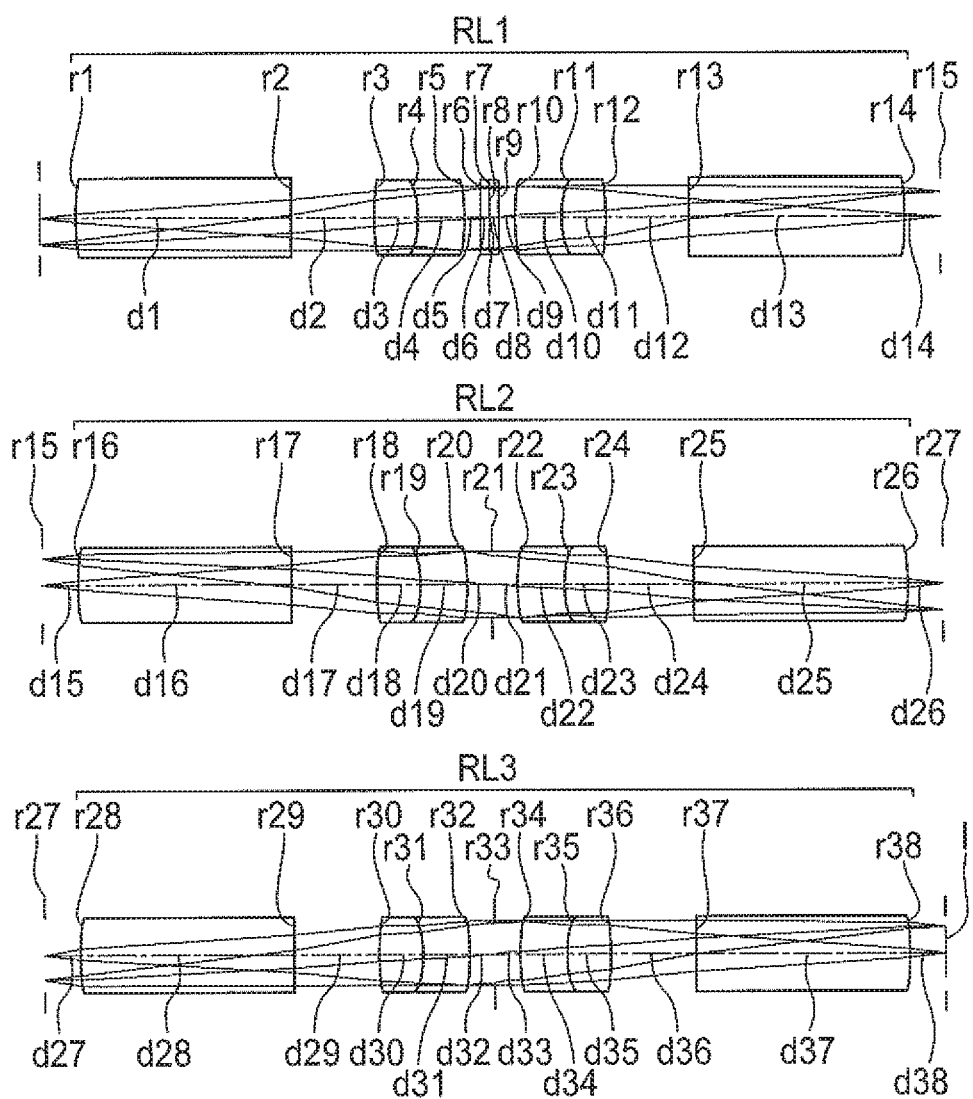
FIG. 13 is a lens cross-sectional view of an image relay unit of an example 1.
Figure 15:
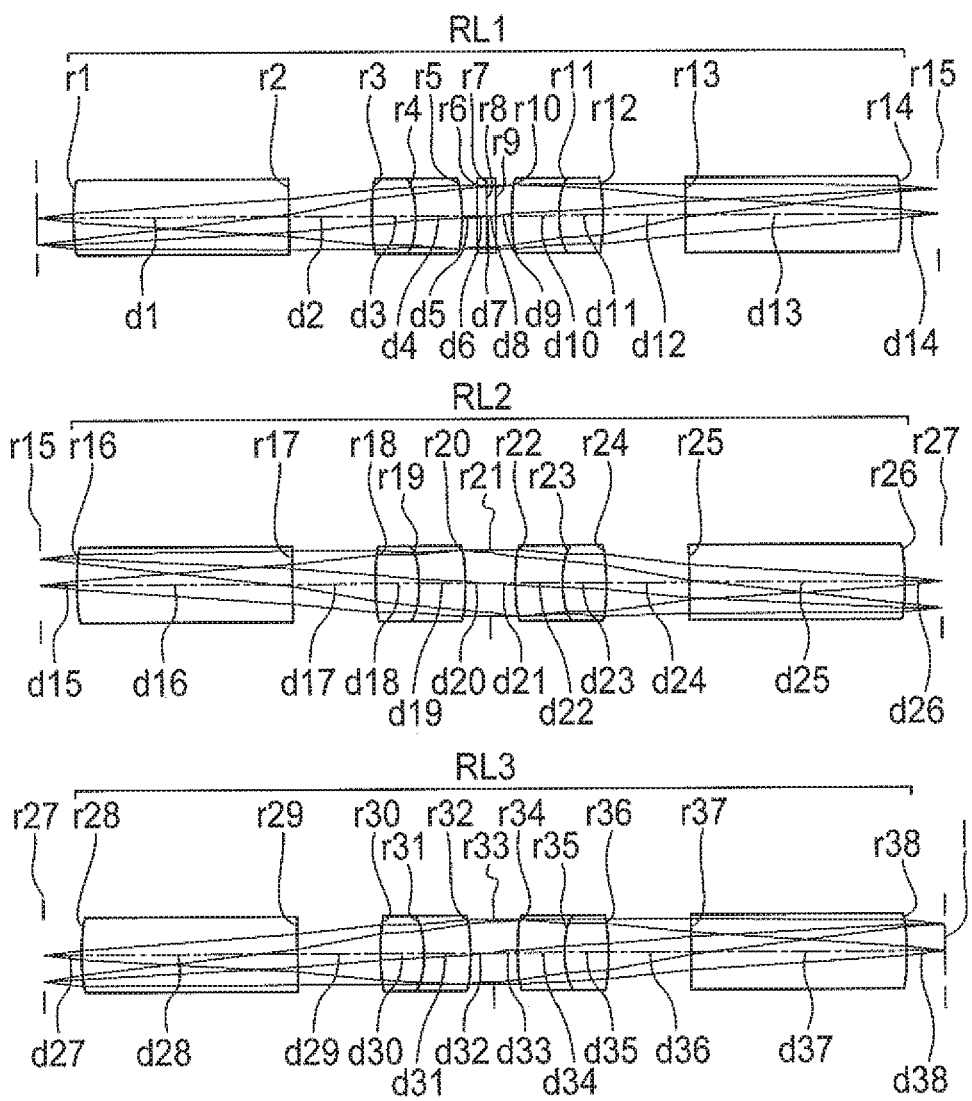
FIG. 15 is a lens cross-sectional view of an image relay unit of an example 2.

Examples of the image relay unit will be described below. FIG. 13 and FIG. 15 are lens cross-sectional views of image relay units of the examples.

Figure 14:
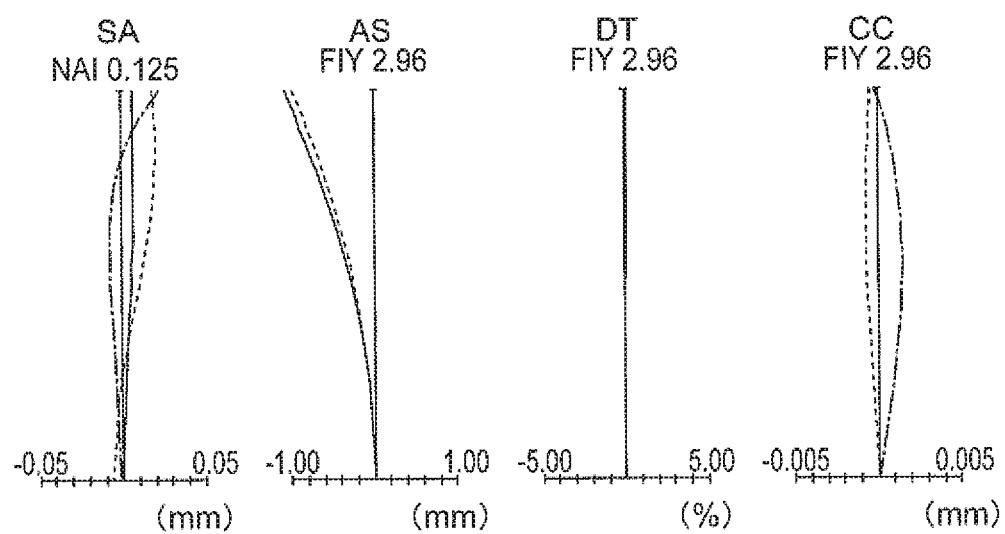
FIG. 14A, FIG. 14B, FIG. 14C, and FIG. 14D are aberration diagrams of the image relay unit of the example 1.
Figures 16A, 16B, 16C, 16D:
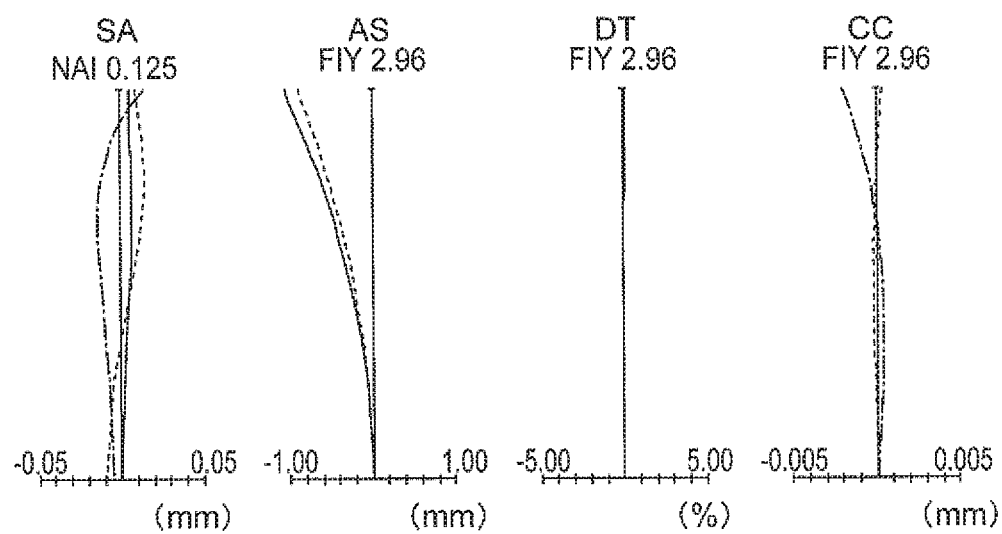
FIG. 16A, FIG. 16B, FIG. 16C, and FIG. 16d are aberration diagrams of the image relay unit of the example 2.

Aberration diagrams of examples of the optical system for rigid endoscope will be described below. FIG. 14A and FIG. 16A show a spherical aberration (SA), FIG. 14B and FIG. 16B show an astigmatism (AS), FIG. 14C and FIG. 16C show a distortion (DT), and FIG. 14D and FIG. 16D show a chromatic aberration of magnification.

An image relay unit of an example 1 includes a first relay optical system RL1, a second relay optical system RL2, and a third relay optical system RL3. The first relay optical system RL1 includes a diffractive optical element. Both the second relay optical system RL2 and the third relay optical system RL3 consist of lenses. Therefore, no diffractive optical element is disposed in the second relay optical system RL2 and the third relay optical system RL3.

A primary image (not shown in the diagram) is relayed by the first relay optical system. Accordingly, a first relay image (not shown in the diagram) is formed. The first relay image is relayed by the second relay optical system RL2. Accordingly, a second relay image (not shown in the diagram) is formed. The second relay image is relayed by the third relay optical system RL3. Accordingly, a third relay image I is formed.

An image relay unit of an example 2 includes a first relay optical system RL1, a second relay optical system RL2, and a third relay optical system RL3. The first relay optical system RL1 includes a diffractive optical element. Both the second relay optical system RL2 and the third relay optical system RL3 consist of lenses. Therefore, no diffractive optical element is disposed in the second relay optical system RL2 and the third relay optical system RL3.

A primary image (not shown in the diagram) is relayed by the first relay optical system. Accordingly, a first relay image (not shown in the diagram) is formed. The first relay image is relayed by the second relay optical system RL2. Accordingly, a second relay image (not shown in the diagram) is formed. The second relay image is relayed by the third relay optical system RL3. Accordingly, a third relay image I is formed.

Figure 17:
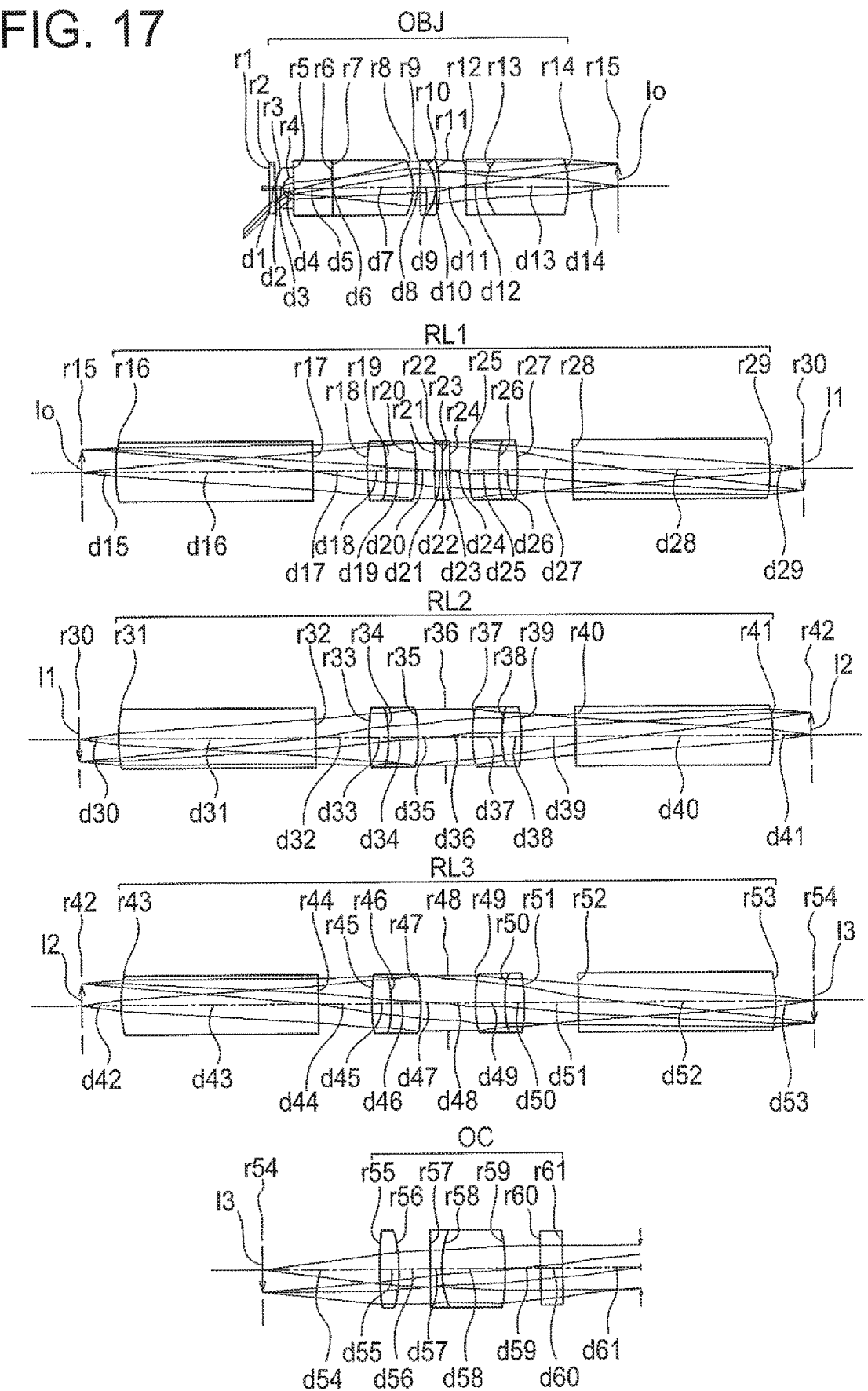
FIG. 17 is a lens cross-sectional view of an optical system for rigid endoscope of an example 1.
Figure 19:
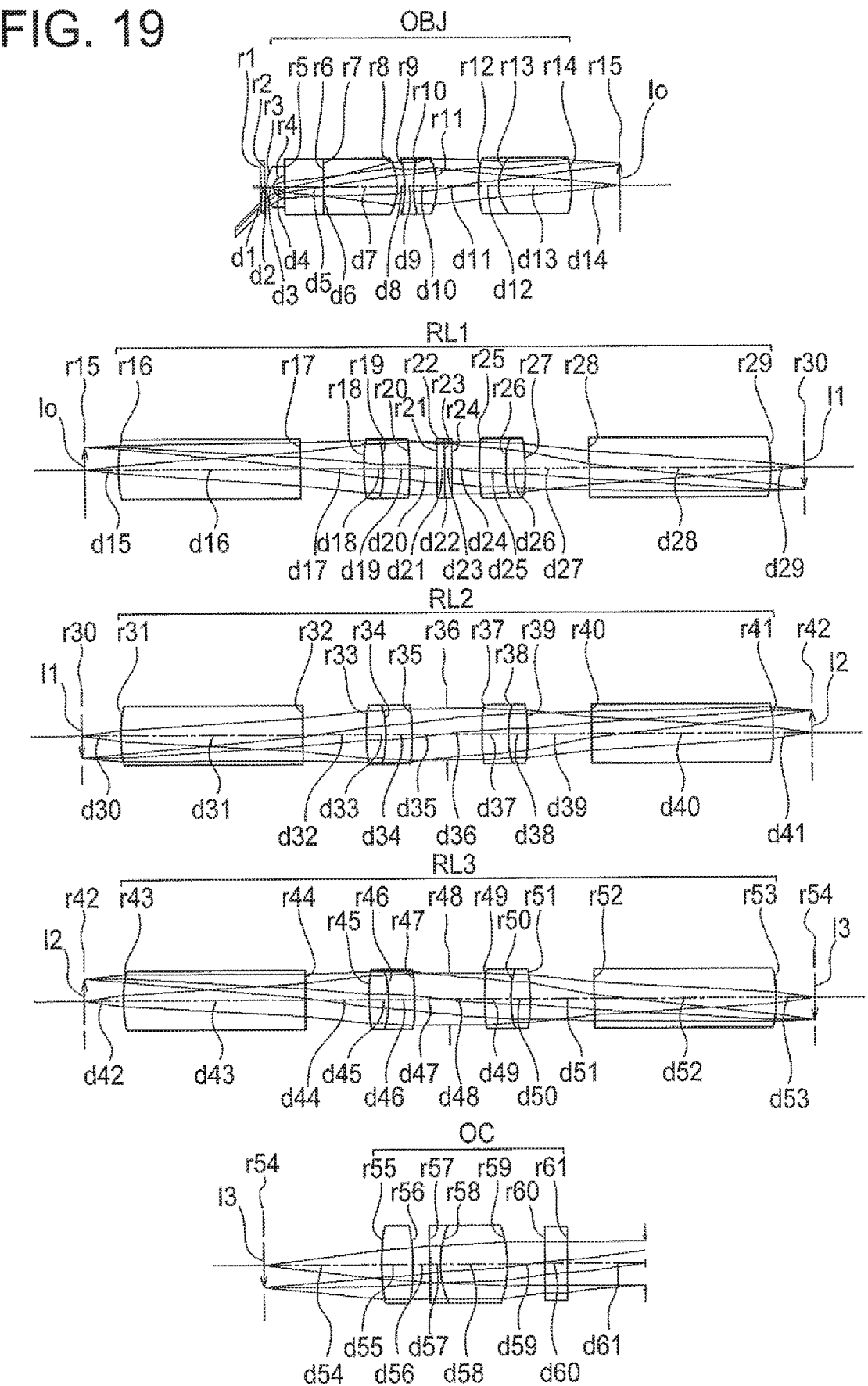
FIG. 19 is a lens cross-sectional view of an optical system for rigid endoscope of an example 2.
Figure 21:
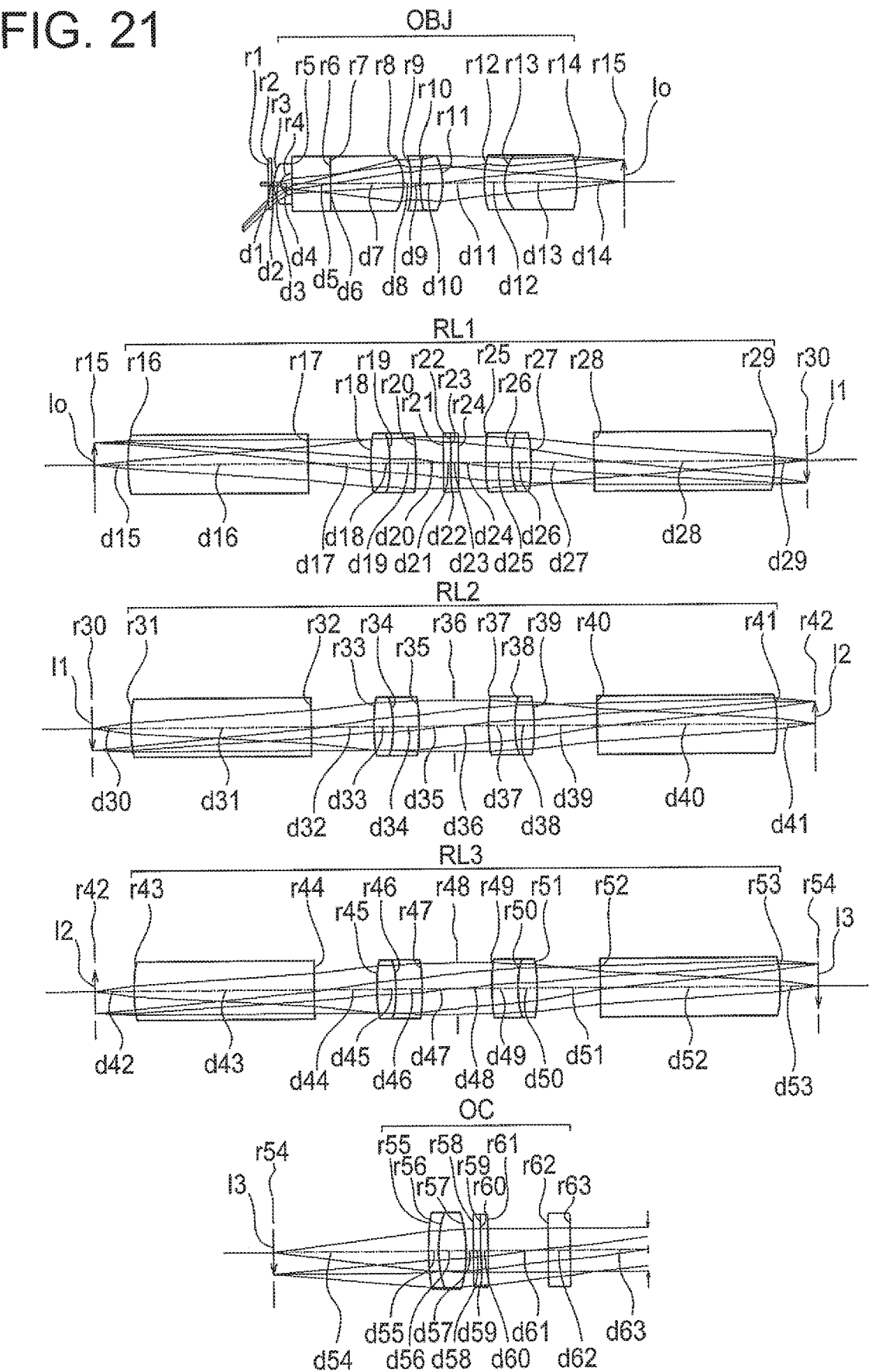
FIG. 21 is a lens cross-sectional view of an optical system for rigid endoscope of an example 3.

Examples of the optical system for rigid endoscope will be described below. FIG. 17, FIG. 19, and FIG. 21 are lens cross-sectional views of optical systems for rigid endoscope of the examples.

Figure 18:
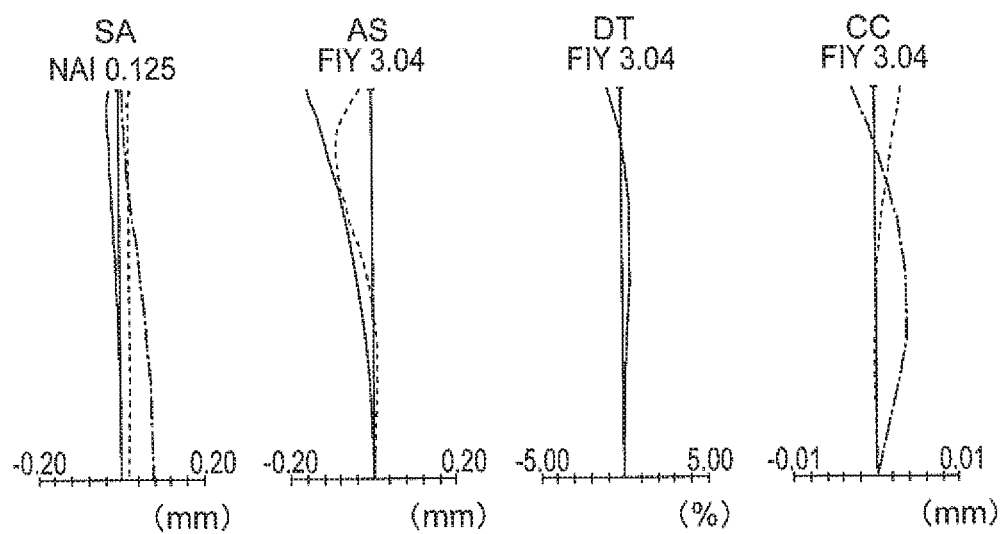
FIG. 18A, FIG. 18B, FIG. 18C, and FIG. 18D are aberration diagrams of the optical system for rigid endoscope of the example 1.
Figures 20A, 20B, 20C, 20D:
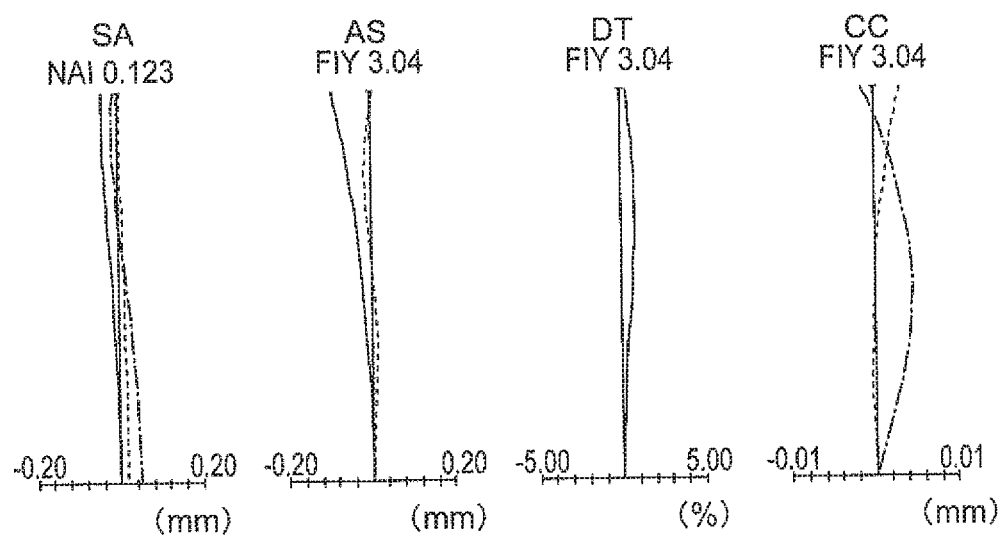
FIG. 20A, FIG. 20B, FIG. 20C, and FIG. 20D are aberration diagrams of the optical system for rigid endoscope of the example 2.
Figure 22:
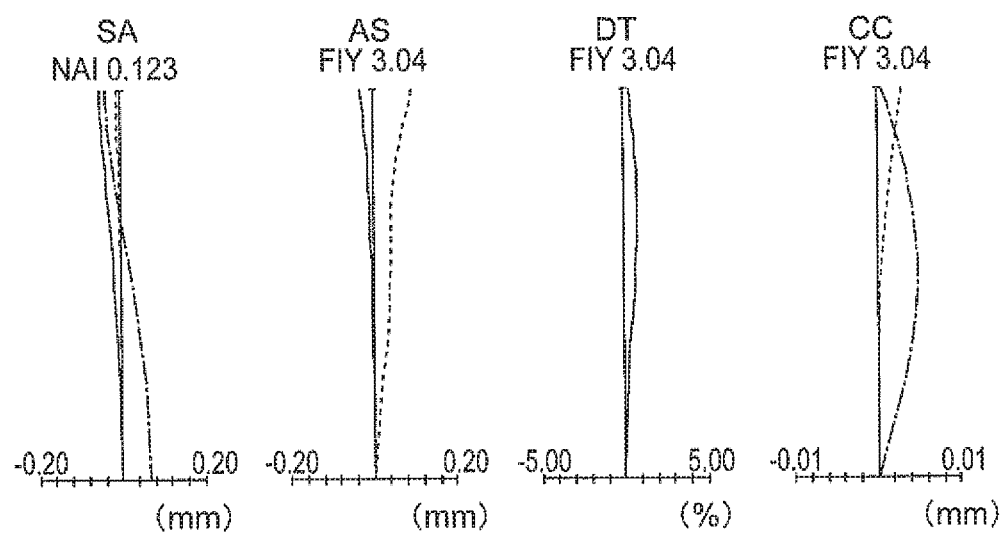
FIG. 22A, FIG. 22B, FIG. 22C, and FIG. 22D are aberration diagrams of the optical system for rigid endoscope of the example 3.

Aberration diagrams of the examples of the optical system for rigid endoscope will be described below. FIG. 18A, FIG. 20A, and FIG. 22A show a spherical aberration (SA), FIG. 18B, FIG. 20B, and FIG. 22B show an astigmatism (AS), FIG. 18C, FIG. 20C, and FIG. 22C show a distortion (DT), and FIG. 18D, FIG. 20D, and FIG. 22D show a chromatic aberration of magnification. The aberrations show an aberration when light emerged from an eyepiece optical system forms an image by an aplanatic lens. Optical specifications of the aplanatic lens are same as optical specifications of the eyepiece optical system.

An optical system for rigid endoscope of an example 1 includes an objective optical system OBJ, an image relay unit, and an eyepiece optical system OC. The image relay unit includes a first relay optical system RL1, a second relay optical system RL2, and a third relay optical system RL3.

Both the objective optical system OBJ and the eyepiece optical system OC consist of lenses. Therefore, no diffractive optical element is disposed in the objective optical system OBJ and the eyepiece optical system OC.

The first relay optical system RL1 includes a diffractive optical element. Both the second relay optical system RL2 and the third relay optical system RL3 consist of lenses. Therefore, no diffractive optical element is disposed in the second relay optical system RL2 and the third relay optical system RL3.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. It is possible to observe the third relay image I3 by the eyepiece optical system OC.

An optical system for rigid endoscope of an example 2 includes an objective optical system OBJ, an image relay unit, and an eyepiece optical system OC. The image relay unit includes a first relay optical system RL1, a second relay optical system RL2, and a third relay optical system RL3.

Both the objective optical system OBJ and the eyepiece optical system OC consist of lenses. Therefore, no diffractive optical element is disposed in the objective optical system OBJ and the eyepiece optical system OC.

The first relay optical system RL1 includes a diffractive optical element. Both the second relay optical system RL2 and the third relay optical system RL3 consist of lenses. Therefore, no diffractive optical element is disposed in the second relay optical system RL2 and the third relay optical system RL3.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. It is possible to observe the third relay image I3 by the eyepiece optical system OC.

An optical system for rigid endoscope of an example 3 includes an objective optical system OBJ, an image relay unit, and an eyepiece optical system OC. The image relay unit includes a first relay optical system RL1, a second relay optical system RL2, and a third relay optical system RL3.

The objective optical system OBJ consist of lenses. Therefore, no diffractive optical element is disposed in the objective optical system OBJ. The eyepiece optical system OC includes a diffractive optical element.

The first relay optical system RL1 includes a diffractive optical element. Both the second relay optical system RL2 and the third relay optical system RL3 consist of lenses. Therefore, no diffractive optical element is disposed in the second relay optical system RL2 and the third relay optical system RL3.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. It is possible to observe the third relay image I3 by the eyepiece optical system OC.

Numerical data of each example described above is shown below. In Surface data, r denotes radius of curvature of each lens surface, d denotes a distance between respective lens surfaces, nd denotes a refractive index of each lens for a d-line, νd denotes an Abbe number for each lens, * denotes an aspherical surface, and # denotes a diffractive surface. LA denotes the first lens, LB denotes the second lens.

Moreover, in various data, NA denotes the numerical aperture. In the examples of the relay optical system, f denotes a focal length of the relay optical system, $\theta gF_{LA}$ denotes the partial dispersion ratio, OBH denotes the maximum object height, IH denotes the maximum image height, and Φce denotes a light-ray effective diameter. In the example of the image relay unit, f denotes a focal length of the image relay unit. In the example of the optical system for rigid endoscope, f denotes a focal length of the optical system for rigid endoscope, ω denotes a half angle of view, fOB denotes a focal length of the objective optical system, fRL denotes a focal length of the relay optical system, and fOC denotes a focal length of the eyepiece optical system.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . .

$$Z=(y^2/r)/[1+\{1-(1+k)(y/r)^2\}^{1/2}]+A4y^4+A6y^6+A8y^8+A10y^{10}+A12y^{12}+\ldots$$

Further, in the aspherical surface coefficients, 'e-n' (where, n is an integral number) indicates '$10^{-n}$'.

Moreover, a diffractive surface, based on high refractive index method, is indicated as an aspheric-surface shape of an equivalent ultrahigh index lens (refracting lens having an extremely high refractive index). The following relationship is established between a pitch d of a diffraction grating formed on the diffractive surface and the aspheric-surface shape of the ultrahigh index lens.

$$d=m\lambda/[(n-1)\{ch/(1-c^2(1+k)h^2)^{1/2}+2A_2h+4A_4h^3+6A_6h^5+8A_8h^7+10A_{10}h^9+\}]$$

Example 1

Unit mm

Surface data

| Surface no. | r | d | nd | νd |
|---|---|---|---|---|
| Object plane | ∞ | 7.00 | | |
| 1 | 24.495 | 21.18 | 1.69895 | 30.13 |
| 2 | 282.066 | 0.57 | | |
| 3 | 30.752 | 15.82 | 1.49700 | 81.54 |
| 4 | −8.230 | 9.38 | 1.78590 | 44.20 |
| 5 | −17.490 | 1.79 | | |
| 6 | ∞ | 1.00 | 1.63387 | 23.37 |
| 7# | 3444935.194 | 0.00 | 1001.00000 | −3.45 |
| 8 | ∞ | 1.00 | 1.69534 | 36.44 |
| 9 | ∞ | 1.79 | | |
| 10 | 17.490 | 9.38 | 1.78590 | 44.20 |
| 11 | 8.230 | 15.82 | 1.49700 | 81.54 |
| 12 | −30.752 | 0.57 | | |
| 13 | −282.066 | 21.18 | 1.69895 | 30.13 |
| 14 | −24.495 | 7.00 | | |
| Image plane | ∞ | | | |

Diffractive surface data

7th surface k = 0.000
A4 = −7.79204e−10, A6 = 3.08304e−11

Various data

| f | 6218.78 |
|---|---|
| NA | 0.12 |
| OBH | 3.0 |
| IH | 3.0 |
| φdoe | 7.4 |

Example 2

Unit mm

Surface data

| Surface no. | r | d | nd | νd |
|---|---|---|---|---|
| Object plane | ∞ | 7.00 | | |
| 1 | 29.342 | 21.37 | 1.95906 | 17.47 |
| 2 | −91.638 | 0.93 | | |
| 3 | −81.086 | 13.86 | 1.49700 | 81.54 |
| 4 | −7.089 | 10.83 | 1.67270 | 32.10 |
| 5 | −16.373 | 1.76 | | |
| 6 | ∞ | 1.00 | 1.63387 | 23.37 |
| 7# | 4138344.045 | 0.00 | 1001.00000 | −3.45 |
| 8 | ∞ | 1.00 | 1.69534 | 36.44 |
| 9 | ∞ | 1.76 | | |
| 10 | 16.373 | 10.83 | 1.67270 | 32.10 |
| 11 | 7.089 | 13.86 | 1.49700 | 81.54 |
| 12 | 81.086 | 0.93 | | |
| 13 | 91.638 | 21.37 | 1.95906 | 17.47 |
| 14 | −29.342 | 7.00 | | |
| Image plane | ∞ | | | |

Diffractive surface data

7th surface k = 0.000
A4 = −1.70043e−09, A6 = 3.20830e−11

Various data

| f | 7324.68 |
|---|---|
| NA | 0.12 |
| OBH | 3.0 |
| IH | 3.0 |
| φdoe | 7.4 |

Example 3

Unit mm

Surface data

| Surface no. | r | d | nd | vd |
|---|---|---|---|---|
| Object plane | ∞ | 6.00 | | |
| 1 | 18.735 | 12.28 | 1.69895 | 30.13 |
| 2 | 43.745 | 6.27 | | |
| 3 | 19.755 | 12.12 | 1.49700 | 81.54 |
| 4 | −7.194 | 9.50 | 1.78590 | 44.20 |
| 5 | −16.546 | 1.67 | | |
| 6 | ∞ | 1.00 | 1.63387 | 23.37 |
| 7# | 28155387.954 | 0.00 | 1001.00000 | −3.45 |
| 8 | ∞ | 1.00 | 1.69534 | 36.44 |
| 9 | ∞ | 1.67 | | |
| 10 | 16.546 | 9.50 | 1.78590 | 44.20 |
| 11 | 7.194 | 12.12 | 1.49700 | 81.54 |
| 12 | −19.755 | 6.27 | | |
| 13 | −43.745 | 12.28 | 1.69895 | 30.13 |
| 14 | −18.735 | 6.00 | | |
| Image plane | ∞ | | | |

Diffractive surface data

7th surface k = 0.000
A4 = −2.16611e−09, A6 = 7.23326e−11

Various data

| f | 4731.10 |
|---|---|
| NA | 0.13 |
| OBH | 3.0 |
| IH | 3.0 |
| φdoe | 7.4 |

Example 4

Unit mm

Surface data

| Surface no. | r | d | nd | vd |
|---|---|---|---|---|
| Object plane | ∞ | 5.98 | | |
| 1 | 16.971 | 27.02 | 1.58913 | 61.14 |
| 2 | ∞ | 0.50 | | |
| 3* | 22.220 | 6.02 | 1.43875 | 94.93 (LB) |
| 4 | −9.172 | 7.29 | 1.83400 | 37.16 |
| 5 | −16.838 | 2.03 | | |
| 6(Stop) | ∞ | 2.03 | | |
| 7 | 16.838 | 7.29 | 1.83400 | 37.16 |
| 8 | 9.172 | 6.02 | 1.43875 | 94.93 |
| 9* | −22.220 | 0.50 | | |
| 10 | ∞ | 27.02 | 1.58913 | 61.14 |
| 11 | −16.971 | 5.98 | | |
| Image plane | ∞ | | | |

Aspherical surface data

3rd surface k = 0.000
A4 = −4.49167e−05, A6 = 6.92624e−07, A8 = −2.78252e−08

9th surface k = 0.000
A4 = 4.49167e−05, A6 = −6.92624e−07, A8 = 2.78252e−08

Various data

| f | 2743.06 |
|---|---|
| NA | 0.14 |
| OBH | 3.0 |
| IH | 3.0 |

Example 5

Unit mm

Surface data

| Surface no. | r | d | nd | vd |
|---|---|---|---|---|
| Object plane | ∞ | 6.03 | | |
| 1 | 17.749 | 27.45 | 1.58913 | 61.14 |
| 2 | ∞ | 2.78 | | |
| 3 | 21.527 | 3.38 | 1.43875 | 94.93 (LB) |
| 4 | −8.888 | 0.80 | 1.63387 | 23.38 (LA) |
| 5* | −8.671 | 4.73 | 1.80625 | 40.91 |
| 6 | −16.392 | 3.69 | | |
| 7(Stop) | ∞ | 3.69 | | |
| 8 | 16.392 | 4.73 | 1.80625 | 40.91 |
| 9* | 8.671 | 0.80 | 1.63387 | 23.38 |
| 10 | 8.888 | 3.38 | 1.43875 | 94.93 |
| 11 | −21.527 | 2.78 | | |
| 12 | ∞ | 27.45 | 1.58913 | 61.14 |
| 13 | −17.749 | 6.03 | | |
| Image plane | ∞ | | | |

Aspherical surface data

5th surface k = 0.000
A4 = −3.32464e−05, A6 = 5.77541e−07, A8 = −1.73224e−09

9th surface k = 0.000
A4 = 3.32464e−05, A6 = −5.77541e−07, A8 = 1.73224e−09

Various data

| f | 3132.12 |
|---|---|
| NA | 0.14 |
| θgF$_{L4}$ | 0.668 |
| OBH | 3.0 |
| IH | 3.0 |

Example 6

Unit mm

Surface data

| Surface no. | r | d | nd | vd |
|---|---|---|---|---|
| Object plane | ∞ | 5.00 | | |
| 1 | 17.933 | 30.13 | 1.58913 | 61.14 |
| 2 | ∞ | 2.94 | | |
| 3 | 21.755 | 2.87 | 1.49700 | 81.54 (LB) |
| 4 | −9.683 | 0.50 | 1.63387 | 23.38 (LA) |
| 5* | −9.136 | 4.60 | 1.80625 | 40.91 |
| 6 | −19.780 | 2.81 | | |
| 7 (Stop) | ∞ | 2.81 | | |
| 8 | 19.780 | 4.60 | 1.80625 | 40.91 |
| 9* | 9.136 | 0.50 | 1.63387 | 23.38 |

-continued

Unit mm

| | | | | |
|---|---|---|---|---|
| 10 | 9.683 | 2.87 | 1.49700 | 81.54 |
| 11 | −21.755 | 2.94 | | |
| 12 | ∞ | 30.13 | 1.58913 | 61.14 |
| 13 | −17.933 | 5.00 | | |
| Image plane | ∞ | | | |

Aspherical surface data

5th surface k = 0.000
A4 = −3.16714e−05, A6 = 3.81781e−07, A8 = 7.19077e−09
9th surface k = 0.000
A4 = 3.16714e−05, A6 = −3.81781e−07, A8 = −7.19077e−09

Various data

| | |
|---|---|
| f | 3204.50 |
| NA | 0.14 |
| θgF$_{L4}$ | 0.668 |
| OBH | 3.0 |
| IH | 3.0 |

Example 7

Unit mm

Surface data

| Surface no. | r | d | nd | vd |
|---|---|---|---|---|
| Object plane | ∞ | 4.00 | | |
| 1 | 19.916 | 23.04 | 1.58913 | 61.14 |
| 2 | ∞ | 9.26 | | |
| 3 | 23.475 | 4.76 | 1.51633 | 64.14 |
| 4 | −9.623 | 5.00 | 1.80610 | 40.92 |
| 5 | −21.196 | 1.80 | | |
| 6 | ∞ | 1.00 | 1.63387 | 23.37 |
| 7# | 502868.621 | 0.00 | 1001.00000 | −3.45 |
| 8 | ∞ | 1.00 | 1.69534 | 36.44 |
| 9 | ∞ | 1.80 | | |
| 10 | 21.196 | 5.00 | 1.80610 | 40.92 |
| 11 | 9.623 | 4.76 | 1.51633 | 64.14 |
| 12 | −23.475 | 9.26 | | |
| 13 | ∞ | 23.04 | 1.58913 | 61.14 |
| 14 | −19.916 | 4.00 | | |
| 15 | ∞ | 4.00 | | |
| 16 | 19.916 | 23.04 | 1.58913 | 61.14 |
| 17 | ∞ | 9.26 | | |
| 18 | 23.475 | 4.76 | 1.51633 | 64.14 |
| 19 | −9.623 | 5.00 | 1.80610 | 40.92 |
| 20 | −21.196 | 2.80 | | |
| 21 | ∞ | 2.80 | | |
| 22 | 21.196 | 5.00 | 1.80610 | 40.92 |
| 23 | 9.623 | 4.76 | 1.51633 | 64.14 |
| 24 | −23.475 | 9.26 | | |
| 25 | ∞ | 23.04 | 1.58913 | 61.14 |
| 26 | −19.916 | 4.00 | | |
| 27 | ∞ | 4.00 | | |
| 28 | 19.916 | 23.04 | 1.58913 | 61.14 |
| 29 | ∞ | 9.26 | | |
| 30 | 23.475 | 4.76 | 1.51633 | 64.14 |
| 31 | −9.623 | 5.00 | 1.80610 | 40.92 |
| 32 | −21.196 | 2.80 | | |
| 33 | ∞ | 2.80 | | |
| 34 | 21.196 | 5.00 | 1.80610 | 40.92 |
| 35 | 9.623 | 4.76 | 1.51633 | 64.14 |
| 36 | −23.475 | 9.26 | | |
| 37 | ∞ | 23.04 | 1.58913 | 61.14 |
| 38 | −19.916 | 4.00 | | |
| Image plane | ∞ | | | |

-continued

Unit mm

Diffractive surface data
7th surface k = 0.000
A4 = −1.29818e−08, A6 = 2.86207e−10

Various data

| | |
|---|---|
| f | 905.00 |
| NA | 0.13 |

Example 8

Unit mm

Surface data

| Surface no. | r | d | nd | vd |
|---|---|---|---|---|
| Object plane | ∞ | 4.00 | | |
| 1 | 19.941 | 23.29 | 1.58913 | 61.14 |
| 2 | ∞ | 9.11 | | |
| 3 | 22.475 | 4.68 | 1.49700 | 81.54 |
| 4 | −9.312 | 5.00 | 1.77250 | 49.60 |
| 5 | −20.520 | 1.77 | | |
| 6 | ∞ | 1.00 | 1.63387 | 23.37 |
| 7# | 1274101.227 | 0.00 | 1001.00000 | −3.45 |
| 8 | ∞ | 1.00 | 1.69534 | 36.44 |
| 9 | ∞ | 1.77 | | |
| 10 | 20.520 | 5.00 | 1.77250 | 49.60 |
| 11 | 9.312 | 4.68 | 1.49700 | 81.54 |
| 12 | −22.475 | 9.11 | | |
| 13 | ∞ | 23.29 | 1.58913 | 61.14 |
| 14 | −19.941 | 4.00 | | |
| 15 | ∞ | 4.00 | | |
| 16 | 19.941 | 23.29 | 1.58913 | 61.14 |
| 17 | ∞ | 9.11 | | |
| 18 | 22.475 | 4.68 | 1.49700 | 81.54 |
| 19 | −9.312 | 5.00 | 1.77250 | 49.60 |
| 20 | −20.520 | 2.77 | | |
| 21 | ∞ | 2.77 | | |
| 22 | 20.520 | 5.00 | 1.77250 | 49.60 |
| 23 | 9.312 | 4.68 | 1.49700 | 81.54 |
| 24 | −22.475 | 9.11 | | |
| 25 | ∞ | 23.29 | 1.58913 | 61.14 |
| 26 | −19.941 | 4.00 | | |
| 27 | ∞ | 4.00 | | |
| 28 | 19.941 | 23.29 | 1.58913 | 61.14 |
| 29 | ∞ | 9.11 | | |
| 30 | 22.475 | 4.68 | 1.49700 | 81.54 |
| 31 | −9.312 | 5.00 | 1.77250 | 49.60 |
| 32 | −20.520 | 2.77 | | |
| 33 | ∞ | 2.77 | | |
| 34 | 20.520 | 5.00 | 1.77250 | 49.60 |
| 35 | 9.312 | 4.68 | 1.49700 | 81.54 |
| 36 | −22.475 | 9.11 | | |
| 37 | ∞ | 23.29 | 1.58913 | 61.14 |
| 38 | −19.941 | 4.00 | | |
| Image plane | ∞ | | | |

Diffractive surface data
7th surface k = 0.000
A4 = −1.30591e−08, A6 = 3.29578e−10

Various data

| | |
|---|---|
| f | 910.33 |
| NA | 0.13 |

Example 9

Unit mm

Surface data

| Surface no. | r | d | nd | vd |
|---|---|---|---|---|
| 1 | ∞ | 0.70 | 1.76900 | 64.15 |
| 2 | ∞ | 0.20 | | |
| 3* | 4.434 | 0.93 | 1.80610 | 40.92 |
| 4* | 1.026 | 1.47 | | |
| 5 | ∞ | 5.25 | 1.80610 | 40.95 |
| 6 | ∞ | 0.00 | 1.80610 | 40.92 |
| 7 | ∞ | 11.08 | 1.80610 | 40.92 |
| 8* | −6.675 | 0.97 | | |
| 9 | ∞ | 1.82 | 1.49700 | 81.54 |
| 10 | −6.450 | 0.68 | 1.85026 | 32.27 |
| 11 | −11.281 | 3.36 | | |
| 12 | 44.277 | 2.75 | 1.85478 | 24.80 |
| 13 | 6.371 | 10.97 | 1.49700 | 81.54 |
| 14 | −12.247 | 6.84 | | |
| 15 | ∞ | 4.49 | | |
| 16 | 19.018 | 26.45 | 1.58913 | 61.14 |
| 17 | ∞ | 7.40 | | |
| 18 | 23.893 | 2.67 | 1.51633 | 64.14 |
| 19 | −10.169 | 3.84 | 1.88300 | 40.76 |
| 20 | −20.508 | 2.57 | | |
| 21 | ∞ | 1.00 | 1.63387 | 23.38 |
| 22# | 516476.236 | 0.00 | 1001.00000 | −3.45 |
| 23 | ∞ | 1.00 | 1.69534 | 36.44 |
| 24 | ∞ | 2.57 | | |
| 25 | 20.508 | 3.84 | 1.88300 | 40.76 |
| 26 | 10.169 | 2.67 | 1.51633 | 64.14 |
| 27 | −23.893 | 7.40 | | |
| 28 | ∞ | 26.45 | 1.58913 | 61.14 |
| 29 | −19.018 | 4.49 | | |
| 30 | ∞ | 5.24 | | |
| 31 | 19.018 | 26.45 | 1.58913 | 61.14 |
| 32 | ∞ | 7.40 | | |
| 33 | 23.893 | 2.67 | 1.51633 | 64.14 |
| 34 | −10.169 | 3.84 | 1.88300 | 40.76 |
| 35 | −20.508 | 3.57 | | |
| 36 | ∞ | 3.57 | | |
| 37 | 20.508 | 3.84 | 1.88300 | 40.76 |
| 38 | 10.169 | 2.67 | 1.51633 | 64.14 |
| 39 | −23.893 | 7.40 | | |
| 40 | ∞ | 26.45 | 1.58913 | 61.14 |
| 41 | −19.018 | 5.24 | | |
| 42 | ∞ | 5.24 | | |
| 43 | 19.018 | 26.45 | 1.58913 | 61.14 |
| 44 | ∞ | 7.40 | | |
| 45 | 23.893 | 2.67 | 1.51633 | 64.14 |
| 46 | −10.169 | 3.84 | 1.88300 | 40.76 |
| 47 | −20.508 | 3.57 | | |
| 48 | ∞ | 3.57 | | |
| 49 | 20.508 | 3.84 | 1.88300 | 40.76 |
| 50 | 10.169 | 2.67 | 1.51633 | 64.14 |
| 51 | −23.893 | 7.40 | | |
| 52 | ∞ | 26.45 | 1.58913 | 61.14 |
| 53 | −19.018 | 5.24 | | |
| 54 | ∞ | 16.00 | | |
| 55 | 49.886 | 2.47 | 1.43875 | 94.93 |
| 56 | −21.219 | 4.26 | | |
| 57 | 177.760 | 1.48 | 2.00330 | 28.27 |
| 58 | 17.667 | 8.61 | 1.67003 | 47.23 |
| 59 | −21.624 | 4.77 | | |
| 60 | ∞ | 3.00 | 1.76819 | 71.70 |
| 61 | ∞ | 10.50 | | |
| Pupil plane | ∞ | | | |

Aspherical surface data

3rd surface k = −0.028
A4 = −5.63258e−03, A6 = 7.47645e−06

4th surface k = −1.180
A4 = 5.05621e−02, A6 = −3.15431e−03

8th surface k = −0.313
A4 = 1.53854e−04

Diffractive surface data

22th surface k = 0.000
A4 = −1.28409e−08, A6 = 3.13452e−10, A8 = −2.58403e−12

Various data

| | |
|---|---|
| f | 3.06 |
| NA | 0.13 |
| 2ω | 89.80 |
| fOB | 3.01 |
| fRL | 696.82 |
| fOC | 23.27 |

Example 10

Unit mm

Surface data

| Surface no. | r | d | nd | vd |
|---|---|---|---|---|
| 1 | ∞ | 0.70 | 1.76900 | 64.15 |
| 2 | ∞ | 0.20 | | |
| 3* | 4.245 | 0.93 | 1.80610 | 40.92 |
| 4* | 1.011 | 1.46 | | |
| 5 | ∞ | 5.25 | 1.80610 | 40.95 |
| 6 | ∞ | 0.00 | 1.80610 | 40.92 |
| 7 | ∞ | 10.01 | 1.80610 | 40.92 |
| 8* | −6.225 | 0.96 | | |
| 9 | −20.942 | 1.34 | 1.83400 | 37.16 |
| 10 | 15.378 | 3.00 | 1.49700 | 81.54 |
| 11 | −7.897 | 5.82 | | |
| 12 | 22.118 | 2.66 | 1.84666 | 23.78 |
| 13 | 6.545 | 9.64 | 1.49700 | 81.54 |
| 14 | −14.451 | 6.68 | | |
| 15 | ∞ | 4.51 | | |
| 16 | 19.983 | 24.47 | 1.58913 | 61.14 |
| 17 | ∞ | 8.78 | | |
| 18 | 29.777 | 2.56 | 1.65160 | 58.55 |
| 19 | −10.574 | 3.34 | 1.88300 | 40.76 |
| 20 | −28.548 | 3.79 | | |
| 21 | ∞ | 1.00 | 1.63387 | 23.38 |
| 22# | 498691.247 | 0.00 | 1001.00000 | −3.45 |
| 23 | ∞ | 1.00 | 1.69534 | 36.44 |
| 24 | ∞ | 3.79 | | |
| 25 | 28.548 | 3.34 | 1.88300 | 40.76 |
| 26 | 10.574 | 2.56 | 1.65160 | 58.55 |
| 27 | −29.777 | 8.78 | | |
| 28 | ∞ | 24.47 | 1.58913 | 61.14 |
| 29 | −19.983 | 4.51 | | |
| 30 | ∞ | 5.24 | | |
| 31 | 19.983 | 24.47 | 1.58913 | 61.14 |
| 32 | ∞ | 8.78 | | |
| 33 | 29.777 | 2.56 | 1.65160 | 58.55 |
| 34 | −10.574 | 3.34 | 1.88300 | 40.76 |
| 35 | −28.548 | 4.79 | | |
| 36 | ∞ | 4.79 | | |
| 37 | 28.548 | 3.34 | 1.88300 | 40.76 |
| 38 | 10.574 | 2.56 | 1.65160 | 58.55 |
| 39 | −29.777 | 8.78 | | |
| 40 | ∞ | 24.47 | 1.58913 | 61.14 |
| 41 | −19.983 | 5.24 | | |

-continued

Unit mm

| | | | | |
|---|---|---|---|---|
| 42 | ∞ | 5.24 | | |
| 43 | 19.983 | 24.47 | 1.58913 | 61.14 |
| 44 | ∞ | 8.78 | | |
| 45 | 29.777 | 2.56 | 1.65160 | 58.55 |
| 46 | −10.574 | 3.34 | 1.88300 | 40.76 |
| 47 | −28.548 | 4.79 | | |
| 48 | ∞ | 4.79 | | |
| 49 | 28.548 | 3.34 | 1.88300 | 40.76 |
| 50 | 10.574 | 2.56 | 1.65160 | 58.55 |
| 51 | −29.777 | 8.78 | | |
| 52 | ∞ | 24.47 | 1.58913 | 61.14 |
| 53 | −19.983 | 5.24 | | |
| 54 | ∞ | 16.18 | | |
| 55 | 33.647 | 4.14 | 1.43875 | 94.93 |
| 56 | −23.882 | 2.17 | | |
| 57 | 224.243 | 1.49 | 1.83400 | 37.16 |
| 58 | 13.762 | 8.87 | 1.58913 | 61.14 |
| 59 | −19.905 | 5.36 | | |
| 60 | ∞ | 3.00 | 1.76819 | 71.70 |
| 61 | ∞ | 10.50 | | |
| Pupil plane | ∞ | | | |

Aspherical surface data

3rd surface k = 0.114
A4 = −8.32004e−03, A6 = 1.91171e−04

4th surface k = −0.752
A4 = −6.47508e−03, A6 = −7.26821e−03

8th surface k = −0.698
A4 = 2.04648e−04, A6 = −5.61088e−07

Diffractive surface data
22th surface k = 0.000
A4 = −1.22834e−08, A6 = 2.35471e−10

Various data

| | |
|---|---|
| f | 3.12 |
| NA | 0.12 |
| 2ω | 88.00 |
| fOB | 3.07 |
| fRL | 711.85 |
| fOC | 23.30 |

Example 11

Unit mm

Surface data

| Surface no. | r | d | nd | vd |
|---|---|---|---|---|
| 1 | ∞ | 0.70 | 1.76900 | 64.15 |
| 2 | ∞ | 0.20 | | |
| 3* | 4.245 | 0.93 | 1.80610 | 40.92 |
| 4* | 1.011 | 1.46 | | |
| 5 | ∞ | 5.25 | 1.80610 | 40.95 |
| 6 | ∞ | 0.00 | 1.80610 | 40.92 |
| 7 | ∞ | 10.01 | 1.80610 | 40.92 |
| 8* | −6.225 | 0.96 | | |
| 9 | −20.942 | 1.34 | 1.83400 | 37.16 |
| 10 | 15.378 | 3.00 | 1.49700 | 81.54 |
| 11 | −7.897 | 5.82 | | |
| 12 | 22.118 | 2.66 | 1.84666 | 23.78 |
| 13 | 6.545 | 9.64 | 1.49700 | 81.54 |
| 14 | −14.451 | 6.68 | | |
| 15 | ∞ | 4.51 | | |
| 16 | 19.983 | 24.47 | 1.58913 | 61.14 |
| 17 | ∞ | 8.78 | | |
| 18 | 29.777 | 2.56 | 1.65160 | 58.55 |
| 19 | −10.574 | 3.34 | 1.88300 | 40.76 |
| 20 | −28.548 | 3.79 | | |
| 21 | ∞ | 1.00 | 1.63387 | 23.38 |
| 22# | 498691.247 | 0.00 | 1001.00000 | −3.45 |
| 23 | ∞ | 1.00 | 1.69534 | 36.44 |
| 24 | ∞ | 3.79 | | |
| 25 | 28.548 | 3.34 | 1.88300 | 40.76 |
| 26 | 10.574 | 2.56 | 1.65160 | 58.55 |
| 27 | −29.777 | 8.78 | | |
| 28 | ∞ | 24.47 | 1.58913 | 61.14 |
| 29 | −19.983 | 4.51 | | |
| 30 | ∞ | 5.24 | | |
| 31 | 19.983 | 24.47 | 1.58913 | 61.14 |
| 32 | ∞ | 8.78 | | |
| 33 | 29.777 | 2.56 | 1.65160 | 58.55 |
| 34 | −10.574 | 3.34 | 1.88300 | 40.76 |
| 35 | −28.548 | 4.79 | | |
| 36 | ∞ | 4.79 | | |
| 37 | 28.548 | 3.34 | 1.88300 | 40.76 |
| 38 | 10.574 | 2.56 | 1.65160 | 58.55 |
| 39 | −29.777 | 8.78 | | |
| 40 | ∞ | 24.47 | 1.58913 | 61.14 |
| 41 | −19.983 | 5.24 | | |
| 42 | ∞ | 5.24 | | |
| 43 | 19.983 | 24.47 | 1.58913 | 61.14 |
| 44 | ∞ | 8.78 | | |
| 45 | 29.777 | 2.56 | 1.65160 | 58.55 |
| 46 | −10.574 | 3.34 | 1.88300 | 40.76 |
| 47 | −28.548 | 4.79 | | |
| 48 | ∞ | 4.79 | | |
| 49 | 28.548 | 3.34 | 1.88300 | 40.76 |
| 50 | 10.574 | 2.56 | 1.65160 | 58.55 |
| 51 | −29.777 | 8.78 | | |
| 52 | ∞ | 24.47 | 1.58913 | 61.14 |
| 53 | −19.983 | 5.24 | | |
| 54 | ∞ | 21.30 | | |
| 55 | 36.247 | 1.20 | 1.80000 | 29.84 |
| 56 | 14.700 | 3.82 | 1.58913 | 61.14 |
| 57 | −17.353 | 0.84 | | |
| 58 | ∞ | 1.00 | 1.69534 | 36.44 |
| 59 | ∞ | 0.00 | 1001.00000 | −3.45 |
| 60# | −1853495.237 | 1.00 | 1.63387 | 23.38 |
| 61 | ∞ | 8.33 | | |
| 62 | ∞ | 3.00 | 1.76819 | 71.70 |
| 63 | ∞ | 10.50 | | |
| Pupil plane | ∞ | | | |

Aspherical surface data

3rd surface k = 0.114
A4 = −8.32004e−03, A6 = 1.91171e−04

4th surface k = −0.752
A4 = −6.47508e−03, A6 = −7.26821e−03

8th surface k = −0.698
A4 = 2.04648e−04, A6 = −5.61088e−07

Diffractive surface data

22th surface k = 0.000
A4 = −1.22834e−08, A6 = 2.35471e−10

-continued

Unit mm

60th surface k = 0.000
A4 = 7.62271e−09, A6 = −4.36666e−11

Various data

| f | 3.12 |
|---|------|
| NA | 0.12 |
| 2ω | 87.98 |
| fOB | 3.07 |
| fRL | 711.85 |
| fOC | 23.39 |

The values of conditional expressions (1) to (9) in each example are shown below. '-' (hyphen) indicates that there is no corresponding arrangement.

| | Example 1 | Example 2 | Example 3 |
|---|---|---|---|
| (1) Gce/Drel | 0.049 | 0.049 | 0.055 |
| (2) $\beta_{LA}$ | — | — | — |
| (3) $vd_{LA}$ | — | — | — |
| (4) $nd_{LB}$ | — | — | — |
| (5) $vd_{LB}$ | — | — | — |
| (6) Dcd/Drel | 0.107 | 0.120 | 0.125 |
| (7) (OBH + IH)/Φdoe | 0.804 | 0.804 | 0.804 |
| (8) FLdoe/(Φdoe × 100) | 5.047 | 6.062 | 4.130 |
| (9) FLce/Gce | 6.542 | 9.210 | 5.710 |

| | Example 4 | Example 5 | Example 6 |
|---|---|---|---|
| (1) Gce/Drel | 0.042 | 0.075 | 0.057 |
| (2) $\beta_{LA}$ | — | 0.71 | 0.71 |
| (3) $vd_{LA}$ | — | 23.38 | 23.38 |
| (4) $nd_{LB}$ | — | 1.43875 | 1.49700 |
| (5) $vd_{LB}$ | — | 94.93 | 81.54 |
| (6) Dcd/Drel | 0.095 | 0.086 | 0.076 |
| (7) (OBH + IH)/Φdoe | — | — | — |
| (8) FLdoe/(Φdoe × 100) | — | — | — |
| (9) FLce/Gce | 8.335 | 4.537 | 5.721 |

Values of the parameters of each example are shown below.

| | Example 1 | Example 2 | Example 3 |
|---|---|---|---|
| Drel | 113.5 | 113.5 | 97.7 |
| Dcd | 12.2 | 13.6 | 12.2 |
| FLdoe | 3709.2 | 4455.8 | 3035.7 |
| FLce | 36.5 | 50.9 | 30.5 |
| Gce | 9.6 | 5.5 | 5.3 |

| | Example 4 | Example 5 | Example 6 |
|---|---|---|---|
| Drel | 97.7 | 97.7 | 97.7 |
| Dcd | 9.3 | 8.4 | 7.4 |
| FLdoe | — | — | — |
| FLce | 33.8 | 33.4 | 32.1 |
| Gce | 4.1 | 7.4 | 5.6 |

Figure 23:
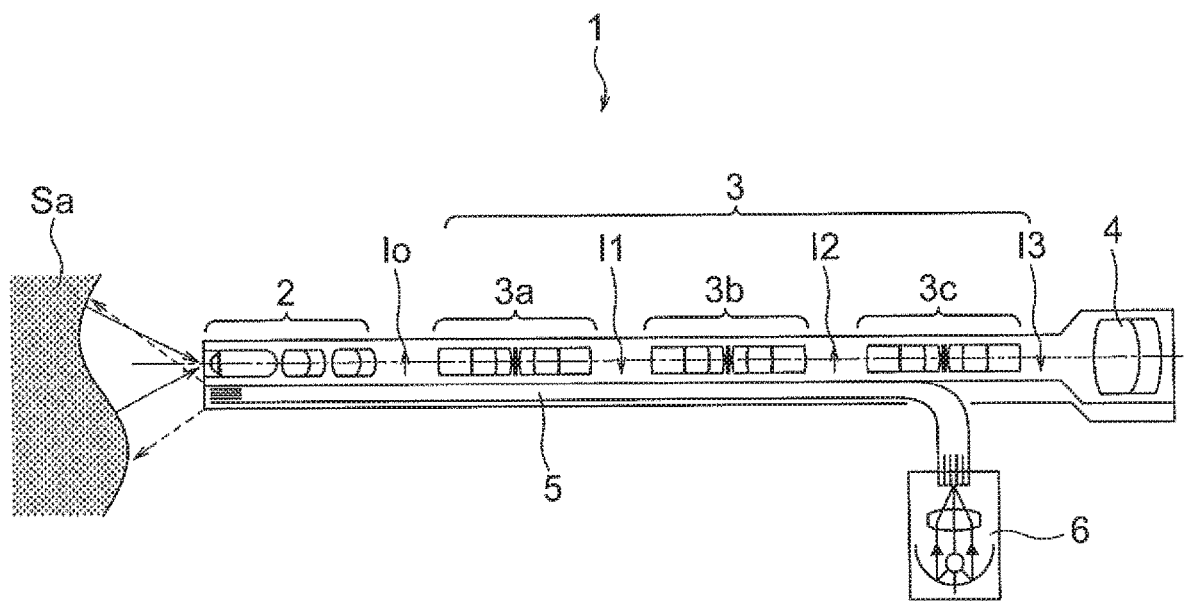
FIG. 23 is a schematic structural diagram of a rigid endoscope.

An example of a rigid endoscope will be described below. FIG. 23 is a schematic structural view of the rigid endoscope. A rigid endoscope 1 includes an objective optical system 2, an image relay unit 3, and an eyepiece optical system 4. Furthermore, the rigid endoscope 1 includes a light guide 5 and an illuminating-unit light source 6.

The image relay unit 3 includes a first relay optical system 3a, a second relay optical system 3b, and a third relay optical system 3c. The relay optical system of the example 1 is used for three relay optical systems.

Illuminating light is emerged from the illuminating-unit light source 6. The illuminating light, upon passing through the light guide 5, is emerged from a front end of the rigid endoscope. Accordingly, the illuminating light is irradiated to an observation object Sa.

A primary image Io of the observation object Sa is formed by the objective optical system 1. The primary image Io is relayed by the first relay optical system 3a. Accordingly, a first relay image I1 is formed. The first relay image I1 is relayed by the second relay optical system 3b. Accordingly, a second relay image I2 is formed. The second relay image I2 is relayed by the third relay optical system 3c. Accordingly, a third relay image I3 is formed. It is possible to observe the third relay image I3 by the eyepiece optical system OC.

Figure 24A:
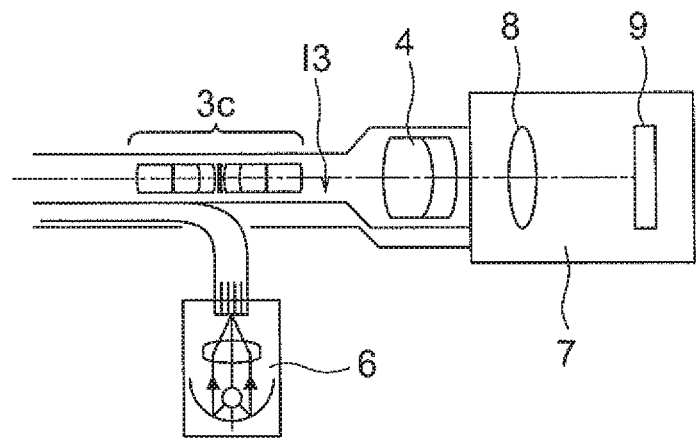
FIG. 24A and FIG. 24B are schematic structural diagrams of an image pickup apparatus.
Figure 24B:
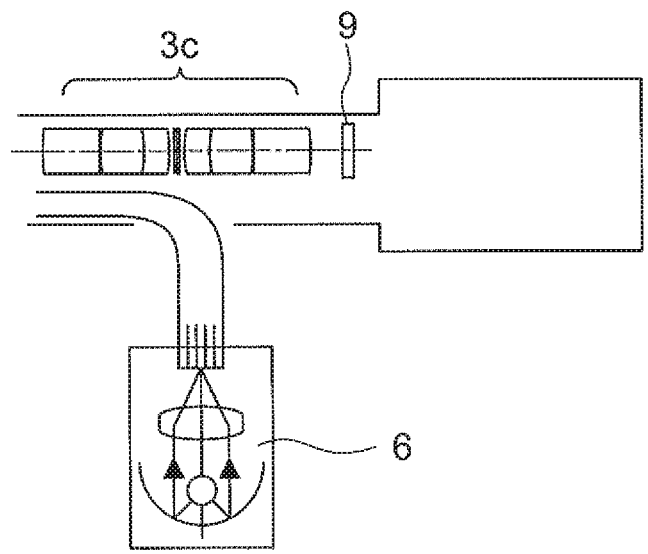

It is possible to capture the third relay image I3 by an image pickup element. FIG. 24A and FIG. 24B are schematic structural views of an image pickup apparatus. FIG. 24A shows an arrangement for capturing via the eyepiece optical system. FIG. 24B shows an arrangement for capturing without passing through the eyepiece optical system.

In the arrangement for capturing passing through the eyepiece optical system, an image pickup unit 7 includes an image forming lens 8 and an image pickup element 9. By the eyepiece optical system 4 and the image forming lens 8, an image of the third relay image I3 is formed on an image pickup surface of the image pickup element 9. By capturing the image by the image pickup element 9, it is possible to acquire an image of the observation object Sa.

In the arrangement for capturing without passing through the eyepiece optical system, the image pickup unit 7 includes the image pickup element 9. The third relay image I3 is formed on an image pickup surface of the image pickup element 9. By capturing the image by the image pickup element 9, it is possible to acquire an image of the observation object Sa.

According to the present embodiment, it is possible to provide a bright relay optical system which has a large numerical aperture and in which the chromatic aberration is corrected favorably, and an optical system for rigid endoscope, and a rigid endoscope in which the relay optical system is used.

As described heretofore, the present invention is suitable for a relay optical system which has a large numerical aperture and in which the chromatic aberration is corrected favorably, and an optical system for rigid endoscope, and a rigid endoscope in which the relay optical system is used.

What is claimed is:

1. A relay optical system, comprising:
   an object-side lens which is disposed nearest to an object;
   an image-side lens which is disposed nearest to an image; and
   a cemented lens having a positive refractive power, wherein:
   the object-side lens has a positive refractive power and is disposed such that a convex surface is directed toward an object side,
   the image-side lens has a positive refractive power, and is disposed such that a convex surface is directed toward an image side,
   a plurality of the cemented lenses are disposed between the object-side lens and the image-side lens,
   a diffractive optical element is disposed between the object-side lens and the image-side lens, and
   the following conditional expression (1) is satisfied:

$$0.04 < Gce/Drel < 0.4 \qquad (1)$$

where,
Gce denotes a smallest interval of intervals of adjacent cemented lenses, and
Drel denotes a distance from an object plane up to an image plane of the relay optical system.

2. The relay optical system according to claim 1, wherein the following conditional expression (6) is satisfied:

$$0.05 < Dcd/Drel < 0.30 \quad (6)$$

where,
Dcd denotes a distance from a cemented surface up to a diffractive surface, and
Drel denotes a distance from the object plane up to the image plane of the relay optical system, and
the cemented surface is a cemented surface of the cemented lens which is positioned nearest to the diffractive optical element.

3. The relay optical system according to claim 1, wherein the following conditional expression (7) is satisfied:

$$0.2 < (OBH+IH)/\Phi doe < 1.2 \quad (7)$$

where,
Φdoe denotes a light-ray effective diameter of the diffractive optical element,
OBH denotes a maximum object height, and
IH denotes a maximum image height.

4. The relay optical system according to claim 1, wherein the following conditional expression (8) is satisfied:

$$0.3 < FLdoe/(\phi doe \times 100) < 15 \quad (8)$$

where,
FLdoe denotes a focal length of the diffractive optical element, and
Φdoe denotes a light-ray effective diameter of the diffractive optical element.

5. The relay optical system according to claim 1, wherein:
the plurality of cemented lenses is disposed in an optical path of the relay optical system, which is formed by an object-side optical path and an image-side optical path,
a lens surface positioned nearest to the image in the object-side optical path is a surface which is convex toward the image side, and
a lens surface positioned nearest to the object in the image-side optical path is a surface which is convex toward the object side.

6. The relay optical system according to claim 1, wherein the following conditional expression (9) is satisfied:

$$1 < FLce/Gce < 20 \quad (9)$$

where,
FLce denotes an average value of focal lengths of the adjacent cemented lenses.

7. An image relay unit, comprising:
a plurality of relay optical systems,
wherein at least one relay optical system of the plurality of relay optical systems is the relay optical system according to claim 1.

8. An image relay unit, comprising:
one or more predetermined relay optical systems; and
a plurality of relay optical systems consisting of lenses,
wherein:
a number of the plurality of relay optical systems consisting of lenses is larger than a number of the one or more predetermined relay optical systems, and
the one or more predetermined relay optical system is the relay optical system according to claim 1, and the following conditional expression (10) is satisfied:

$$0.05 < NAI \times FLdoe/Dreall < 1.5 \quad (10)$$

where,
NAI denotes an image-side numerical aperture of the relay optical system,
FLdoe denotes a focal length of the diffractive optical element, and
Dreall denotes a distance from the object plane up to an image plane of the image relay unit.

9. An optical system for rigid endoscope, comprising:
an objective optical system; and
an image relay unit which is disposed on an image side of the objective optical system,
wherein the image relay unit is the image relay unit according to claim 7.

10. The optical system for rigid endoscope according to claim 9, comprising:
an eyepiece optical system which is disposed on an image side of the image relay unit.

11. A rigid endoscope, comprising:
the optical system for rigid endoscope according to claim 9; and
an image pickup element which captures an image formed by the image relay unit.

12. A rigid endoscope, comprising:
the optical system for rigid endoscope according to claim 10; and
an illuminating unit for illuminating an object to be observed.

13. The rigid endoscope according to claim 11, comprising:
an illuminating unit for illuminating an object to be observed.

14. A relay optical system, comprising:
an object-side lens which is disposed nearest to an object;
an image-side lens which is disposed nearest to an image; and
a cemented lens having a positive refractive power,
wherein:
the object-side lens has a positive refractive power and is disposed such that a convex surface is directed toward an object side,
the image-side lens has a positive refractive power, and is disposed such that a convex surface is directed toward an image side,
a plurality of the cemented lenses are disposed between the object-side lens and the image-side lens,
the following conditional expression (1) is satisfied:

$$0.04 < Gce/Drel < 0.4 \quad (1)$$

where,
Gce denotes a smallest interval of intervals of adjacent cemented lenses, and
Drel denotes a distance from an object plane up to an image plane of the relay optical system,
at least one cemented lens out of the plurality of cemented lenses includes three lenses,
a medium of each of the three lenses is different,
one of the three lenses is a first lens, and
in a rectangular coordinate system in which a horizontal axis is set to be $vd_{LA}$ and a vertical axis is set to be $\theta gF_{LA}$,
when a straight line expressed by $\theta gF_{LA} = \alpha \times vd_{LA} + \beta_{LA}$ is set, where $\alpha = -0.00163$, $\theta gF_{LA}$ and $vd_{LA}$ of a medium of the first lens are included in an area determined by following conditional expression (2) and conditional expression (3):

$$0.64 < \beta_{LA} \qquad (2)$$

$$vd_{LA} < 50 \qquad (3)$$

where, $\theta gF_{LA}$ denotes a partial dispersion ratio $(ng_{LA}-nF_{LA})/(nF_{LA}-nC_{LA})$ of the medium of the first lens, $vd_{LA}$ denotes Abbe number $(nd_{LA}-1)/(nF_{LA}-nC_{LA})$ for the medium of the first lens, and $nd_{LA}$, $nC_{LA}$, $nF_{LA}$, and $ng_{LA}$ denote refractive indices of the medium of the first lens for a d-line, a C-line, an F-line, and a g-line respectively.

15. The relay optical system according to claim 14, wherein:
the cemented lens which includes the first lens, includes a second lens and an aspheric surface, and
the following conditional expressions (4) and (5) are satisfied:

$$1.4 \leq nd_{LB} \leq 1.6 \qquad (4)$$

$$70 \leq vd_{LB} \leq 100 \qquad (5)$$

where, $nd_{LB}$, $nC_{LB}$, and $nF_{LB}$ denote refractive indices of the second lens for the d-line, the C-line, and the F-line respectively, and $vd_{LB}$ denotes Abbe number $(nd_{LB}-1)/(nF_{LB}-nC_{LB})$ for a medium of the second lens.

16. A relay optical system, comprising:
an object-side lens which is disposed nearest to an object;
an image-side lens which is disposed nearest to an image; and
a cemented lens having a positive refractive power, wherein:
the object-side lens has a positive refractive power and is disposed such that a convex surface is directed toward an object side,
the image-side lens has a positive refractive power, and is disposed such that a convex surface is directed toward an image side,
a plurality of the cemented lenses are disposed between the object-side lens and the image-side lens,
the following conditional expression (1) is satisfied:

$$0.04 < Gce/Drel < 0.4 \qquad (1)$$

where,

Gce denotes a smallest interval of intervals of adjacent cemented lenses, and

Drel denotes a distance from an object plane up to an image plane of the relay optical system, at least one cemented lens out of the plurality of cemented lenses includes two lenses,
a medium of each of the two lenses is different,
one of the two lenses is a second lens,
the cemented lens which includes the second lens has an aspheric surface, and
the following conditional expressions (4) and (5) are satisfied:

$$1.4 \leq nd_{LB} \leq 1.6 \qquad (4)$$

$$70 \leq vd_{LB} \leq 100 \qquad (5)$$

where, $nd_{LB}$, $nC_{LB}$, and $nF_{LB}$ denote refractive indices of the second lens for a d-line, a C-line, and an F-line respectively, and $vd_{LB}$ denotes Abbe number $(nd_{LB}-1)/(nF_{LB}-nC_{LB})$ for a medium of the second lens.

* * * * *